US012592090B2

(12) United States Patent
Tran et al.

(10) Patent No.: US 12,592,090 B2
(45) Date of Patent: Mar. 31, 2026

(54) COMPENSATION OF INTENSITY VARIANCES IN IMAGES USED FOR COLONY ENUMERATION

(71) Applicant: NEOGEN FOOD SAFETY US HOLDCO CORPORATION, Lansing, MI (US)

(72) Inventors: Thanh Q. Tran, Blaine, MN (US); Hugh E. Watson, Prior Lake, MN (US); Jitesh N. Joshi, Gujarat (IN); Rinkeshkumar B. Patel, Woodbury, MN (US)

(73) Assignee: NEOGEN FOOD SAFETY US HOLDCO CORPORATION, Lansing, MI (US)

( * ) Notice: Subject to any disclaimer, the term of this patent is extended or adjusted under 35 U.S.C. 154(b) by 252 days.

(21) Appl. No.: 17/904,842

(22) PCT Filed: Apr. 27, 2021

(86) PCT No.: PCT/IB2021/053470
§ 371 (c)(1),
(2) Date: Aug. 23, 2022

(87) PCT Pub. No.: WO2021/229337
PCT Pub. Date: Nov. 18, 2021

(65) Prior Publication Data
US 2023/0142016 A1     May 11, 2023

(30) Foreign Application Priority Data
May 13, 2020     (IN) .............................. 202041020135

(51) Int. Cl.
| | |
|---|---|
| *G06V 20/69* | (2022.01) |
| *C12M 1/34* | (2006.01) |
| *G06V 10/141* | (2022.01) |
| *G06V 10/143* | (2022.01) |
| *G06V 10/25* | (2022.01) |
| *G06V 10/50* | (2022.01) |

(52) U.S. Cl.
CPC ........... *G06V 20/693* (2022.01); *C12M 41/36* (2013.01); *G06V 10/141* (2022.01);
(Continued)

(58) Field of Classification Search
CPC .. G06V 20/693; G06V 10/141; G06V 10/143; G06V 10/25; G06V 10/50; C12M 41/36
See application file for complete search history.

(56) References Cited

U.S. PATENT DOCUMENTS

| | | | |
|---|---|---|---|
| 5,382,782 A | 1/1995 | Hasegawa et al. | |
| 6,774,893 B2 * | 8/2004 | Debiez .................. | G11B 15/68 362/240 |

(Continued)

FOREIGN PATENT DOCUMENTS

| | | | |
|---|---|---|---|
| JP | 6601264 B2 * | 11/2019 | |
| JP | 2022550894 A | 12/2022 | |

(Continued)

OTHER PUBLICATIONS

European Patent Office, JP 2022 550894 A, Patent Translate.

(Continued)

*Primary Examiner* — Stephen R Koziol
*Assistant Examiner* — Joshua Chen
(74) *Attorney, Agent, or Firm* — HYLTON-RODIC LAW PLLC

(57) ABSTRACT

Embodiments described herein involve determining an area of interest on a growth media. An overall brightness control value for a plurality of illumination sources configured to illuminate the growth media is calculated. The overall brightness control value generating at least one image that substantially matches a target intensity at the area of interest. An individual brightness value for each illumination source of the plurality of illumination sources is calculated by individually adjusting a brightness of each illumination (Continued)

source to generate at least one image that substantially matches the target intensity in each respective illumination source's area of influence. A calibrated brightness value for each illumination source is determined based on an image intensity with each illumination source turned on at the respective individual brightness value and an intensity that each illumination source generates within each respective area of influence when turned on alone.

17 Claims, 26 Drawing Sheets

(52) U.S. Cl.
CPC ............ *G06V 10/143* (2022.01); *G06V 10/25* (2022.01); *G06V 10/50* (2022.01)

(56) References Cited

U.S. PATENT DOCUMENTS

| | | | | |
|---|---|---|---|---|
| 10,229,476 | B2 * | 3/2019 | Mendlovic | G01J 3/26 |
| 10,692,216 | B2 * | 6/2020 | Marcelpoil | G06T 7/0016 |
| 10,696,938 | B2 * | 6/2020 | Wiles | G06V 20/698 |

| | | | | | |
|---|---|---|---|---|---|
| 2007/0139638 | A1 | 6/2007 | Wolpert et al. | | |
| 2015/0138504 | A1 * | 5/2015 | Korb | ...................... | A61B 3/101 |
| | | | | | 351/206 |
| 2016/0050736 | A1 * | 2/2016 | Hoang | .................. | F21V 23/005 |
| | | | | | 315/151 |
| 2016/0150238 | A1 * | 5/2016 | Park | ...................... | H04N 19/59 |
| | | | | | 375/240.08 |

FOREIGN PATENT DOCUMENTS

| | | | | |
|---|---|---|---|---|
| TW | | 1468012 | B | * | 1/2015 |
| TW | | I468012 | B | * | 1/2015 |

OTHER PUBLICATIONS

European Patent Office, JP 6601264 B, Patent Translate.
International Searching Authority, International Search Report, Jul. 12, 2021.
Puchalt et al., "Active backlight for automating visual monitoring: An analysis of a lighting control technique for Caenorhabditis elegans cultures on standard Petri plates," PLOS ONE, 14(4), e0215548, Apr. 16, 2019.

* cited by examiner

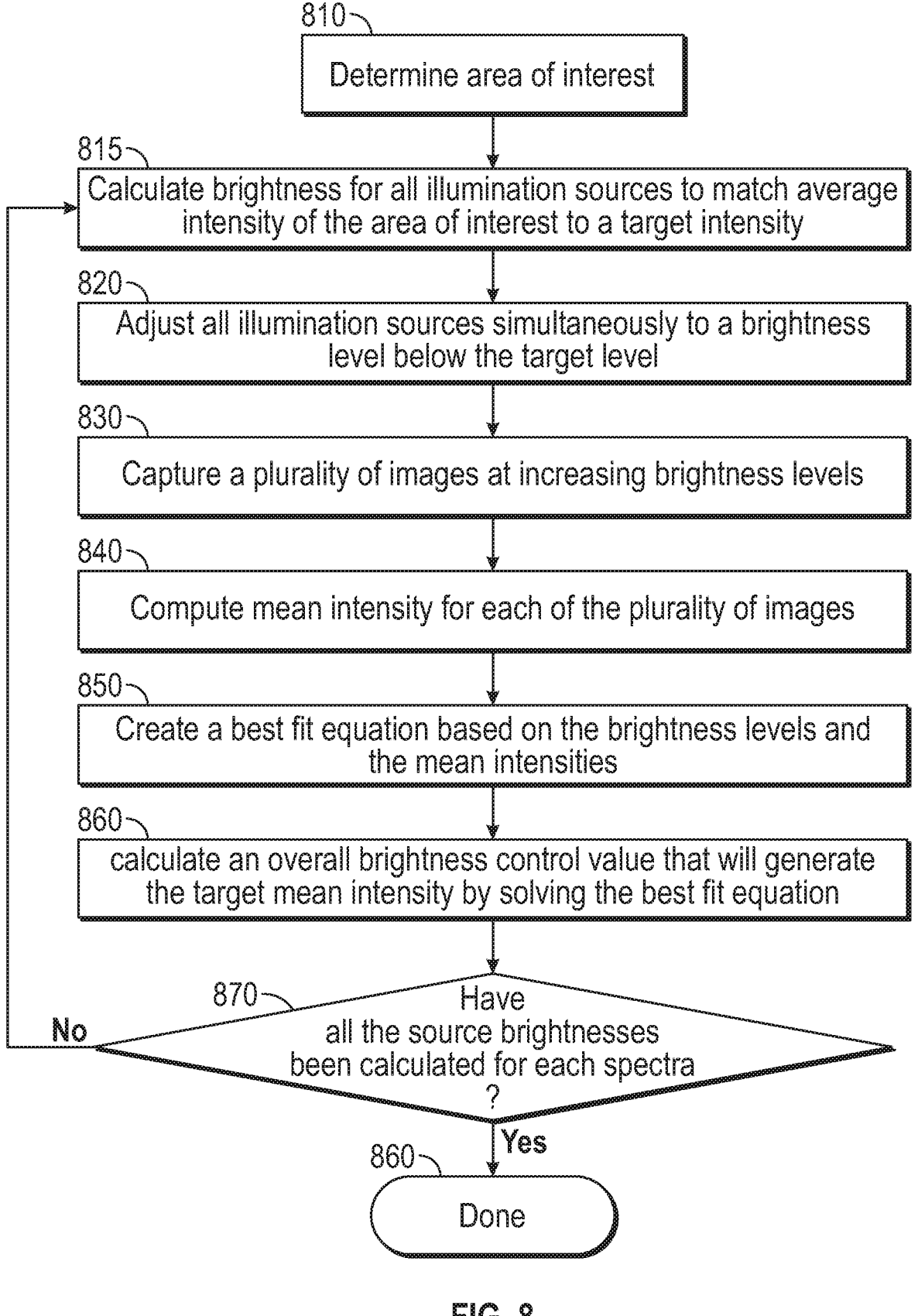

810 — Determine area of interest

815 — Calculate brightness for all illumination sources to match average intensity of the area of interest to a target intensity 820 — Adjust all illumination sources simultaneously to a brightness level below the target level 830 — Capture a plurality of images at increasing brightness levels 840 — Compute mean intensity for each of the plurality of images 850 — Create a best fit equation based on the brightness levels and the mean intensities 860 — calculate an overall brightness control value that will generate the target mean intensity by solving the best fit equation 870 — Have all the source brightnesses been calculated for each spectra ?

No

Yes

860 — Done

FIG. 8

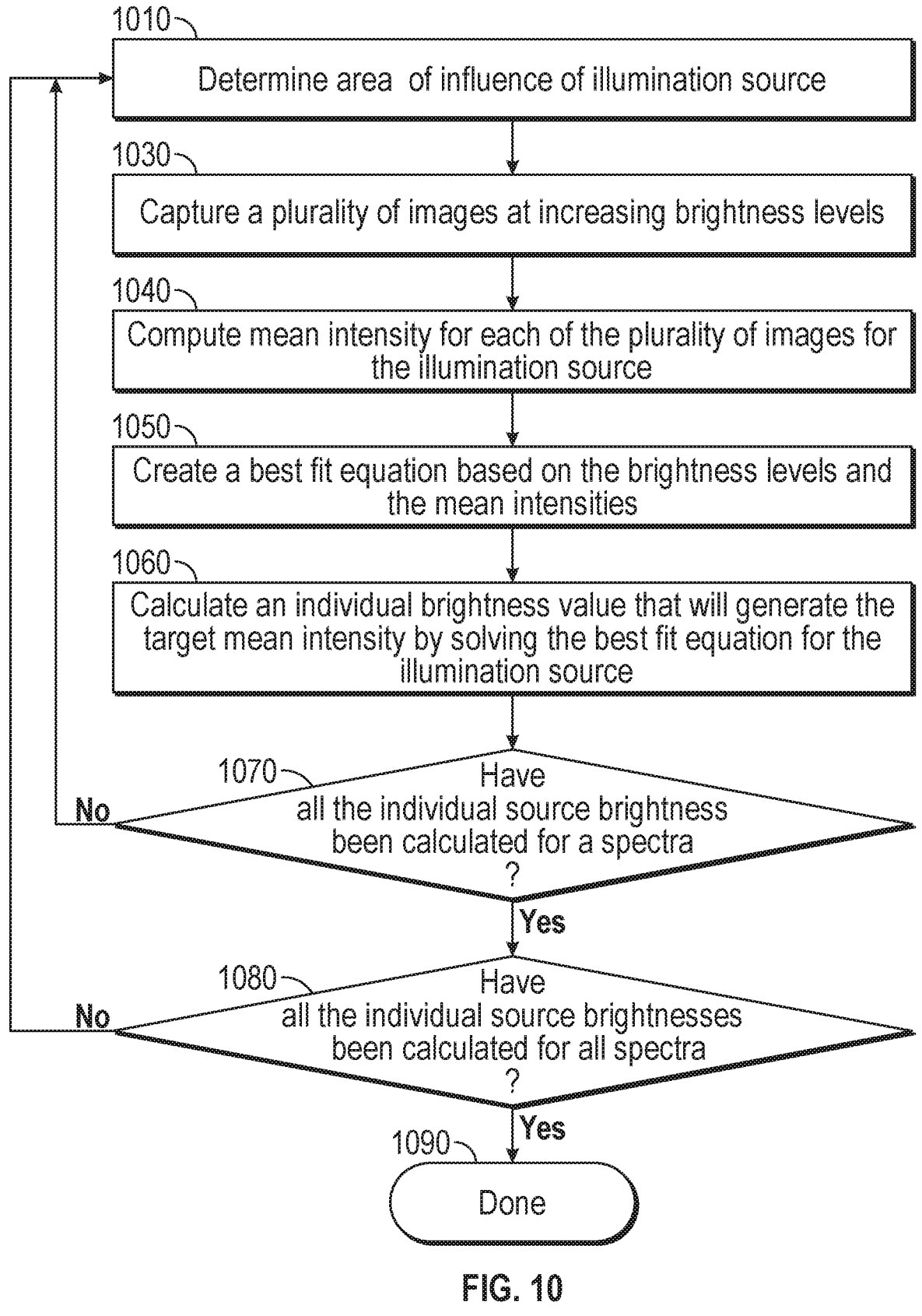

1010 — Determine area of influence of illumination source

1030 — Capture a plurality of images at increasing brightness levels

1040 — Compute mean intensity for each of the plurality of images for the illumination source 1050 — Create a best fit equation based on the brightness levels and the mean intensities 1060 — Calculate an individual brightness value that will generate the target mean intensity by solving the best fit equation for the illumination source 1070 — Have all the individual source brightness been calculated for a spectra ?
No
Yes 1080 — Have all the individual source brightnesses been calculated for all spectra ?
No
Yes 1090 — Done

FIG. 10

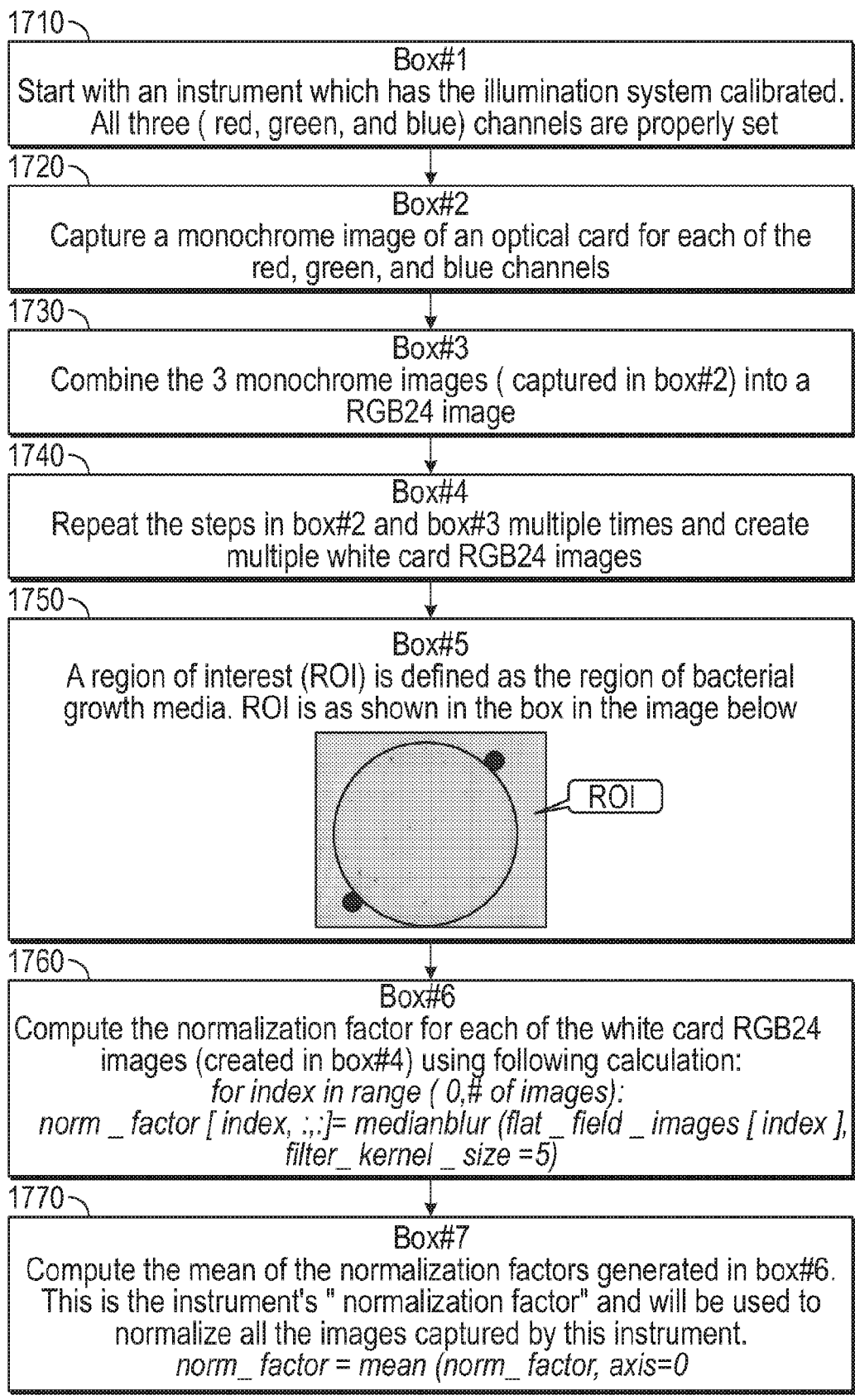

1710

Box#1
Start with an instrument which has the illumination system calibrated. All three ( red, green, and blue) channels are properly set

1720

Box#2
Capture a monochrome image of an optical card for each of the red, green, and blue channels

1730

Box#3
Combine the 3 monochrome images ( captured in box#2) into a RGB24 image

1740

Box#4
Repeat the steps in box#2 and box#3 multiple times and create multiple white card RGB24 images

1750

Box#5
A region of interest (ROI) is defined as the region of bacterial growth media. ROI is as shown in the box in the image below

ROI

1760

Box#6
Compute the normalization factor for each of the white card RGB24 images (created in box#4) using following calculation:
*for index in range ( 0,# of images):*
*norm _ factor [ index, :,:]= medianblur (flat _ field _ images [ index ], filter_ kernel _ size =5)*

1770

Box#7
Compute the mean of the normalization factors generated in box#6. This is the instrument's " normalization factor" and will be used to normalize all the images captured by this instrument.
*norm_ factor = mean (norm_ factor, axis=0*

FIG. 17

Normalization_Factors — 1820

| | | | | |
|---|---|---|---|---|
| 0.8 | 1 | 1.1 | 1 | 0.8 |
| 0.8 | 1 | 1.1 | 1 | 0.8 |
| 0.7 | 1 | 1.2 | 1 | 0.7 |
| 0.8 | 1 | 1.1 | 1 | 0.8 |
| 0.8 | 1 | 1.1 | 1 | 0.8 |

÷

Captured_Image — 1810

| | | | | |
|---|---|---|---|---|
| 176 | 220 | 242 | 220 | 176 |
| 176 | 220 | 242 | 220 | 176 |
| 154 | 220 | 255 | 220 | 154 |
| 176 | 220 | 242 | 220 | 176 |
| 176 | 220 | 242 | 220 | 176 |

Output_Image — 1830

| | | | | |
|---|---|---|---|---|
| 220 | 220 | 220 | 220 | 220 |
| 220 | 220 | 220 | 220 | 220 |
| 220 | 220 | 213 | 220 | 220 |
| 220 | 220 | 220 | 220 | 220 |
| 220 | 220 | 220 | 220 | 220 |

FIG. 18

COMPENSATION OF INTENSITY VARIANCES IN IMAGES USED FOR COLONY ENUMERATION

TECHNOLOGICAL FIELD

The present disclosure is generally related to an imaging device. More particularly, the present disclosure is related to compensation of intensity variances in images.

BACKGROUND

Testing for biological contamination in foods or other materials has become an important and often mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be used to improve biological testing and to streamline and standardize the biological testing process.

Biological growth plates can be used to enumerate or identify the presence of bacteria so that corrective measures can be performed (in the case of food testing) or proper diagnosis can be made (in the case of medical use). In other applications, biological growth plates may be used to rapidly grow bacteria or other biological agents in laboratory samples, e.g., for experimental purposes.

A wide variety of biological growth plates have been developed. As one example, biological growth plates have been developed by 3M Company (hereafter "3M") of St. Paul, Minn. Biological growth plates are sold by 3M under the trade name PETRIFILM plates. Biological growth plates can be utilized to facilitate the rapid growth and detection of bacteria or other biological agents commonly associated with food contamination, including, for example, aerobic bacteria, *E. coli*, coliform, enterobacteriaceae, yeast, mold, Staphylococcus aureus, Listeria, Campylobacter, and the like. The use of PETRIFILM plates, or other growth media, can simplify bacterial testing of food samples.

SUMMARY

Embodiments described herein involve a method comprising determining an area of interest on a growth media. An overall brightness control value for a plurality of illumination sources configured to illuminate the growth media is calculated. The overall brightness control value generates at least one image that substantially matches a target intensity at the area of interest. An individual brightness value for each illumination source of the plurality of illumination sources is calculated based on the overall brightness value by individually adjusting a brightness of each illumination source to generate at least one image that substantially matches the target intensity in each respective illumination source's area of influence. A calibrated brightness value for each illumination source is determined based on an image intensity with each illumination source turned on at the respective individual brightness value and an intensity that each illumination source generates within each respective area of influence when turned on alone.

Embodiments involve a system, comprising a processor and a memory storing computer program instructions which when executed by the processor cause the processor to perform operations. The operations comprise determining an area of interest on a growth media. An overall brightness control value for a plurality of illumination sources configured to illuminate the growth media is calculated. The overall brightness control value generates at least one image that substantially matches a target intensity at the area of interest. An individual brightness value for each illumination source of the plurality of illumination sources is calculated based on the overall brightness value by individually adjusting a brightness of each illumination source to generate at least one image that substantially matches the target intensity in each respective illumination source's area of influence. A calibrated brightness value for each illumination source is determined based on an image intensity with each illumination source turned on at the respective individual brightness value and an intensity that each illumination source generates within each respective area of influence when turned on alone.

Embodiments involve a non-transitory computer readable medium storing computer program instructions for designing microstructures, the computer program instructions when executed by a processor cause the processor to perform operations. The operations comprise determining an area of interest on a growth media. An overall brightness control value for a plurality of illumination sources configured to illuminate the growth media is calculated. The overall brightness control value generates at least one image that substantially matches a target intensity at the area of interest. An individual brightness value for each illumination source of the plurality of illumination sources is calculated based on the overall brightness value by individually adjusting a brightness of each illumination source to generate at least one image that substantially matches the target intensity in each respective illumination source's area of influence. A calibrated brightness value for each illumination source is determined based on an image intensity with each illumination source turned on at the respective individual brightness value and an intensity that each illumination source generates within each respective area of influence when turned on alone.

The above summary is not intended to describe each embodiment or every implementation. Rather, a more complete understanding of illustrative embodiments will become apparent and appreciated by reference to the following Detailed Description of Exemplary Embodiments and claims in view of the accompanying figures of the drawing.

BRIEF DESCRIPTION OF THE DRAWINGS

The present technology may be more completely understood and appreciated in consideration of the following detailed description of various embodiments in connection with the accompanying drawings.

3

Figure 5:
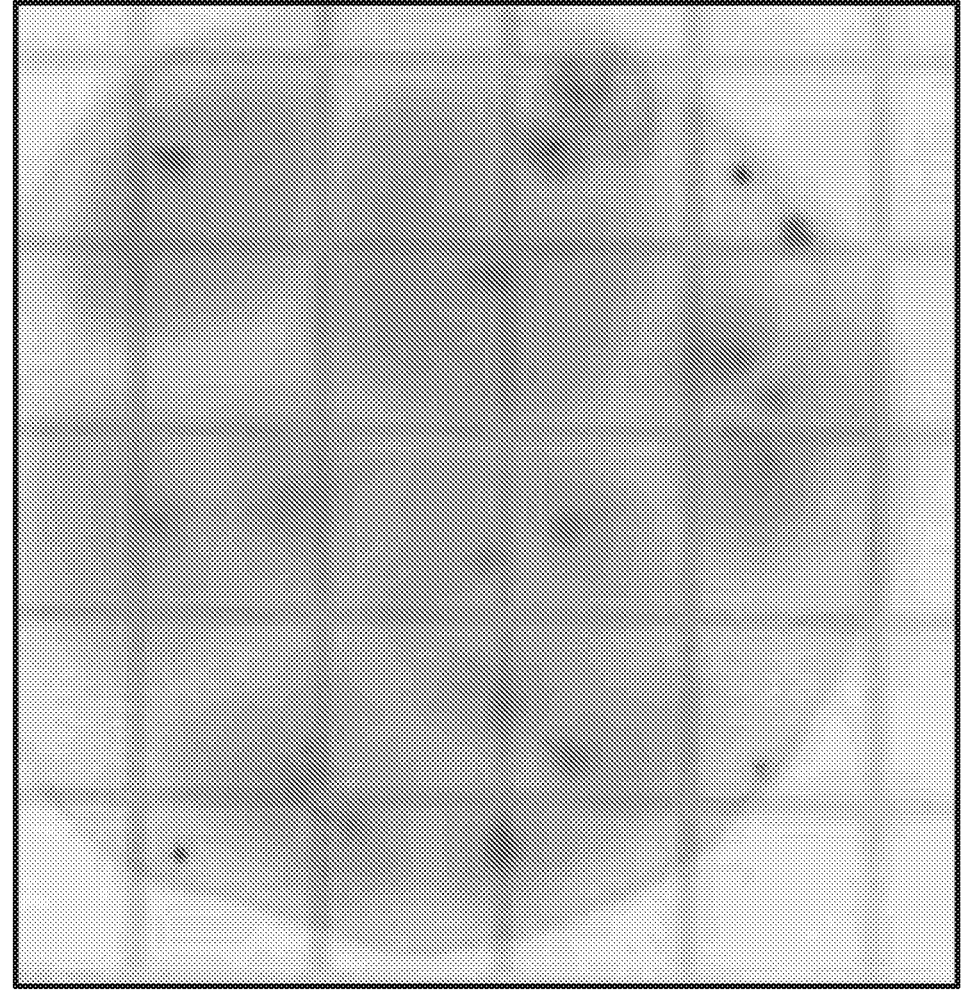
Figure 6A:
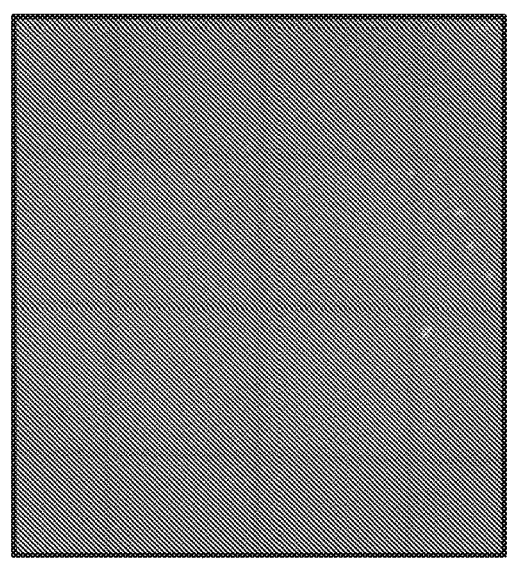
Figure 6B:
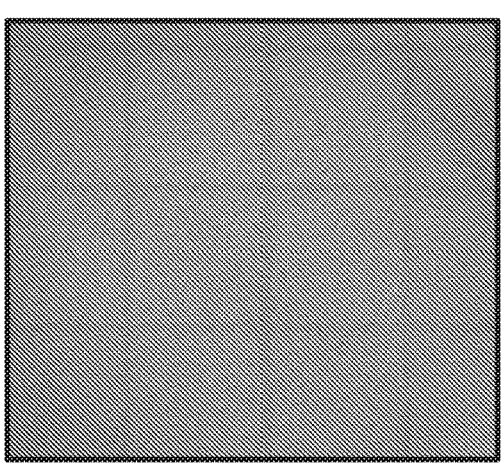
Figure 6C:
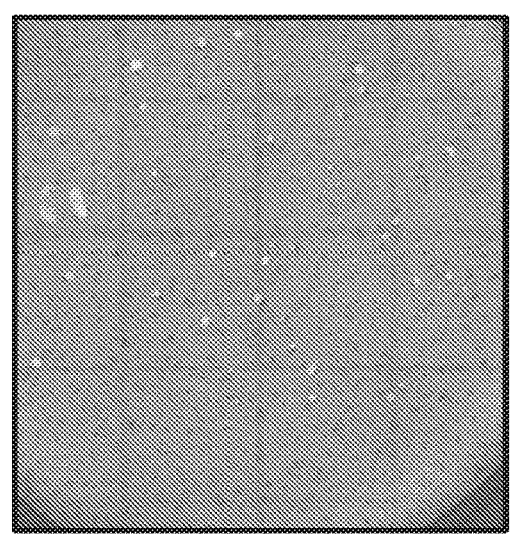
Figure 7:
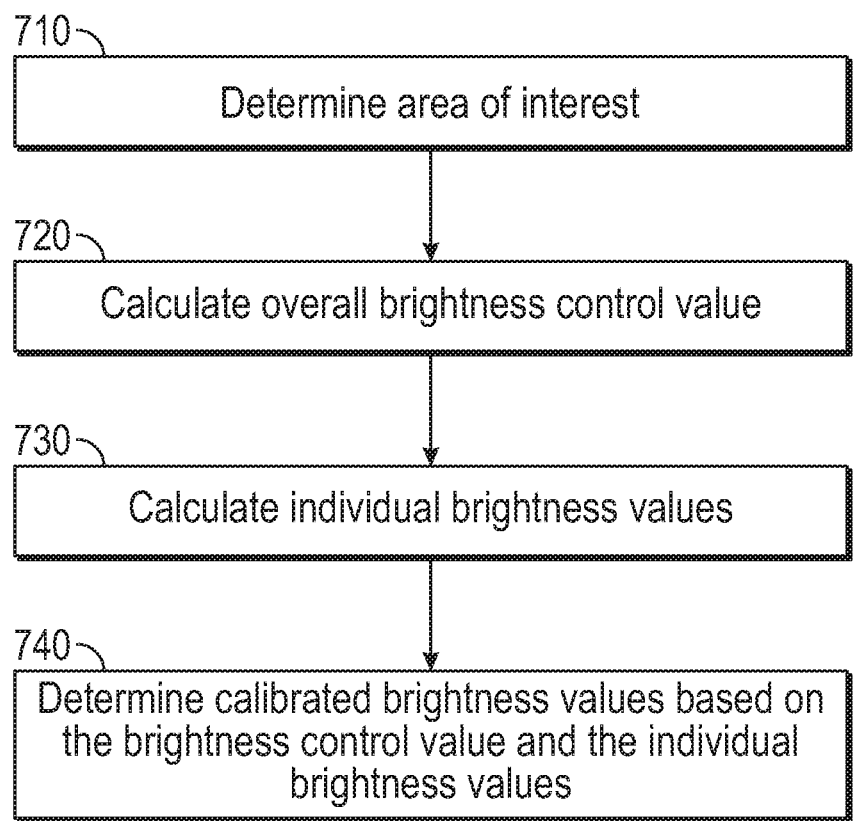
Figure 9:
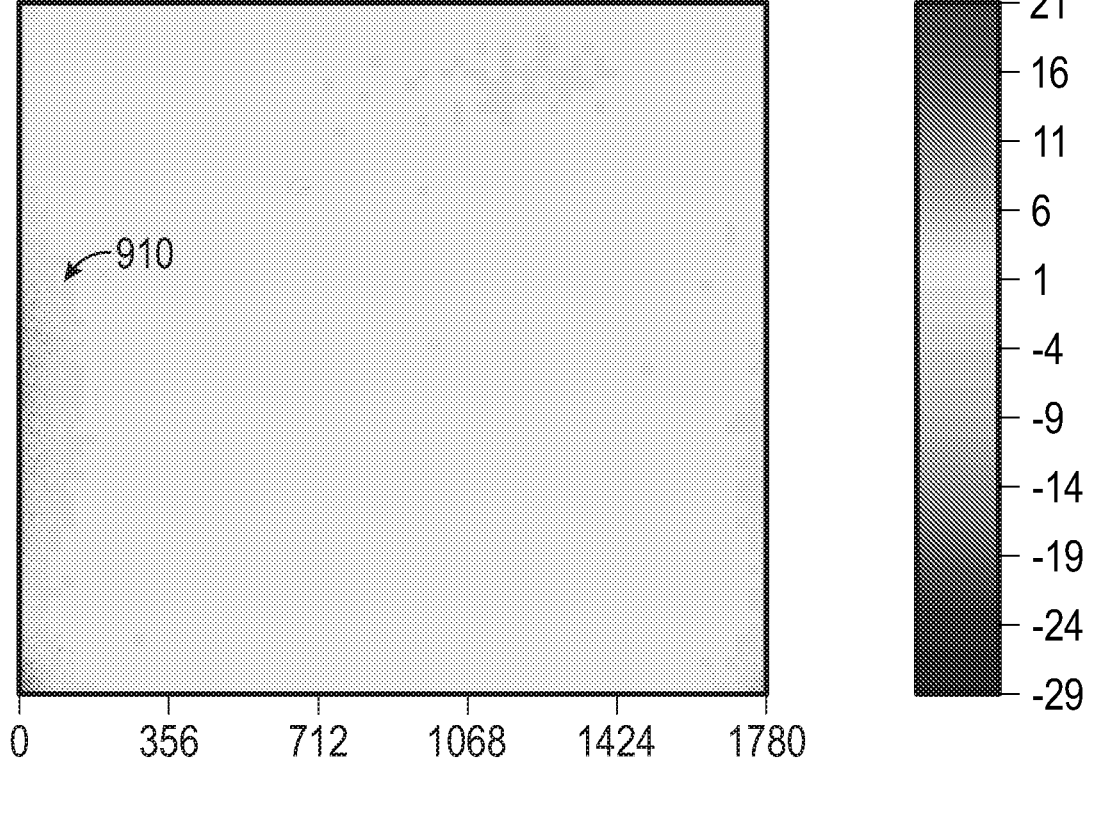
Figure 11A:
Figure 11B:
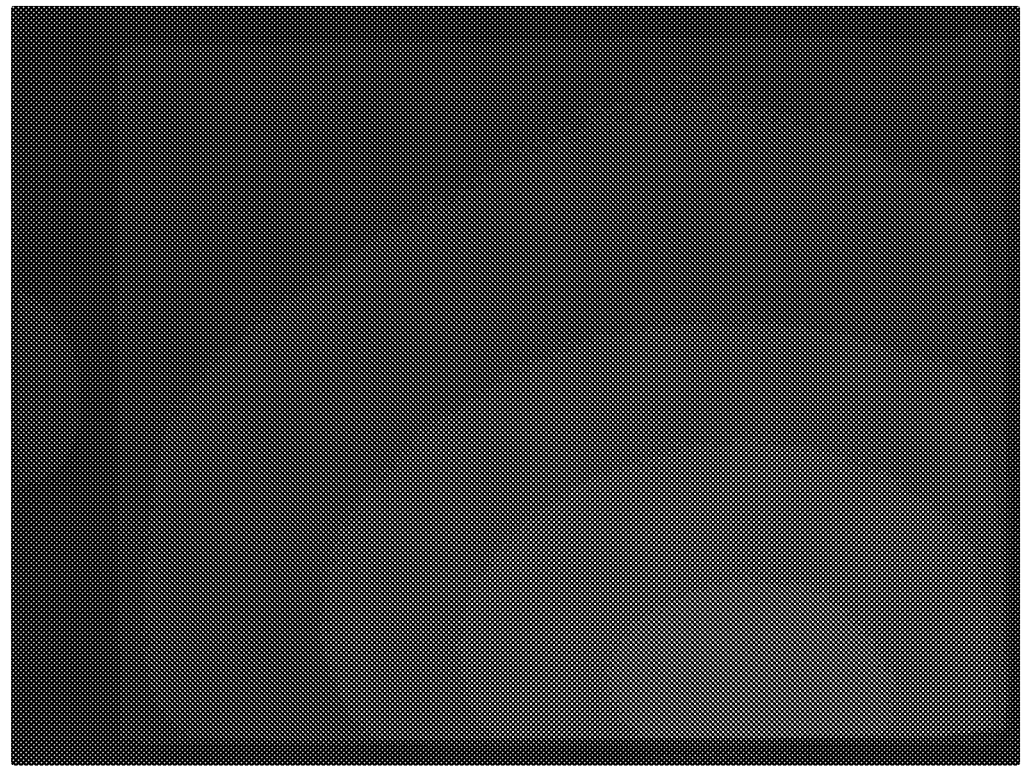
Figure 11C:
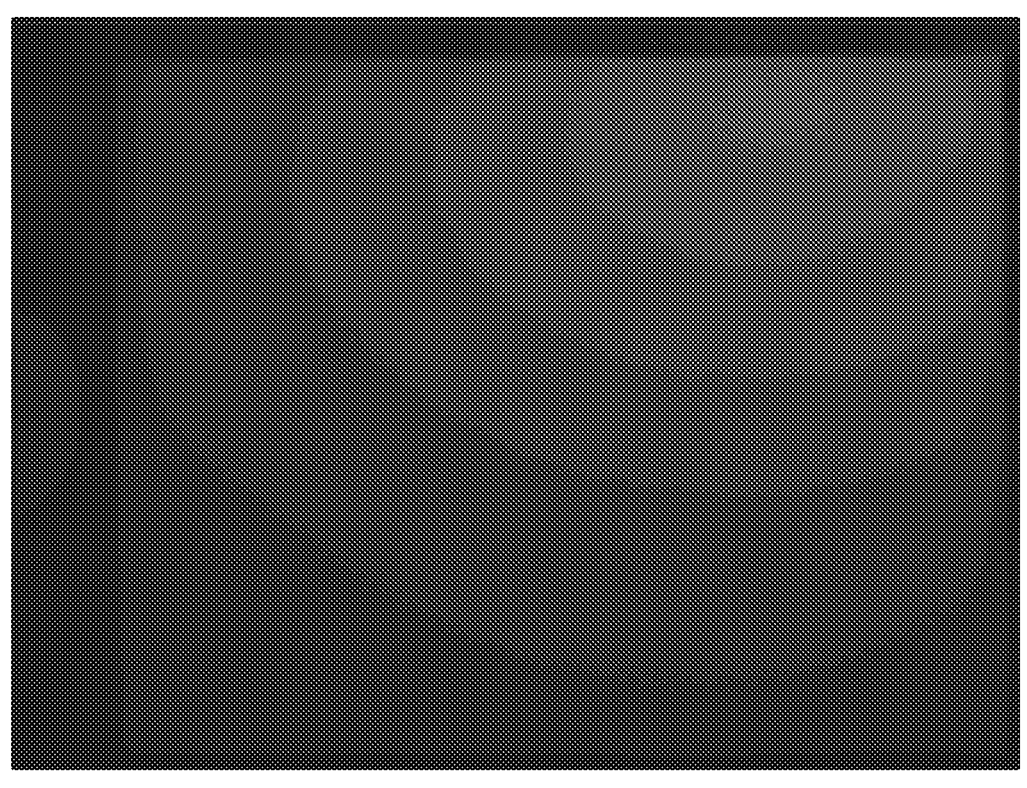
Figure 11D:
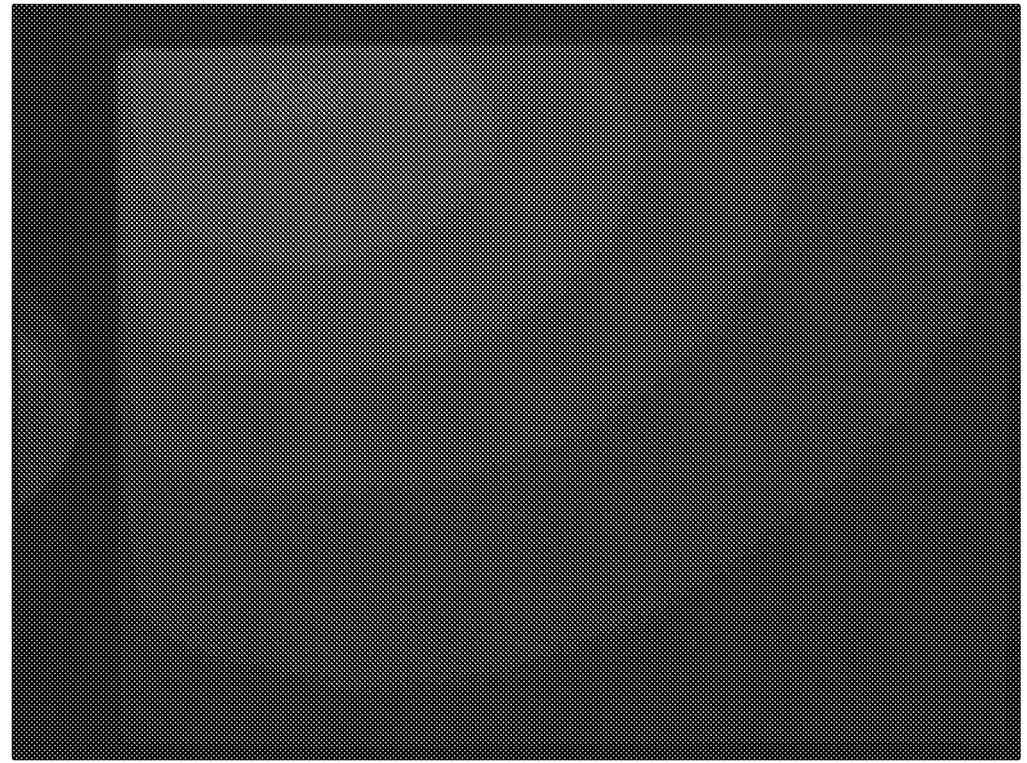
Figure 12:
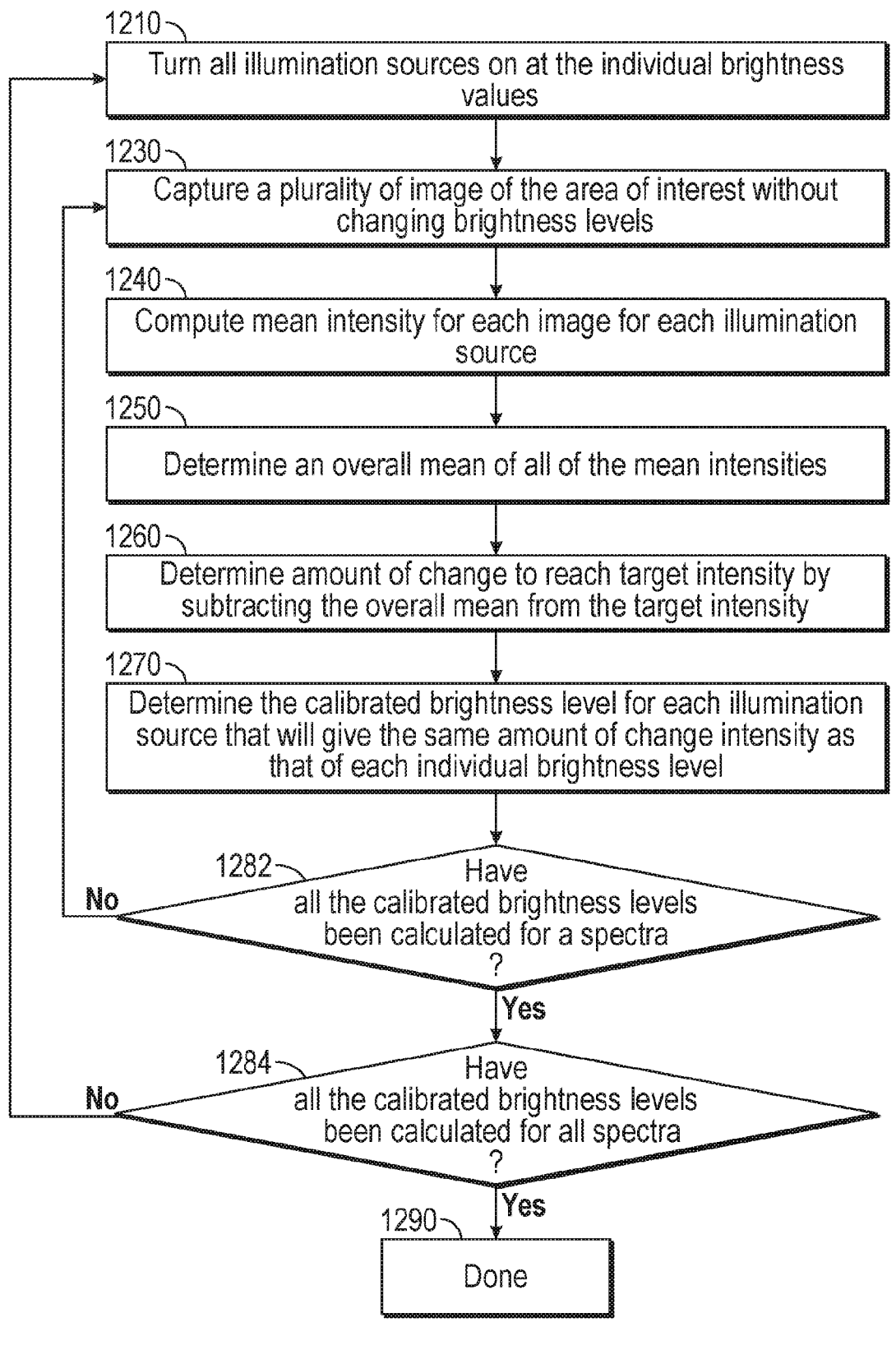
Figure 13A:
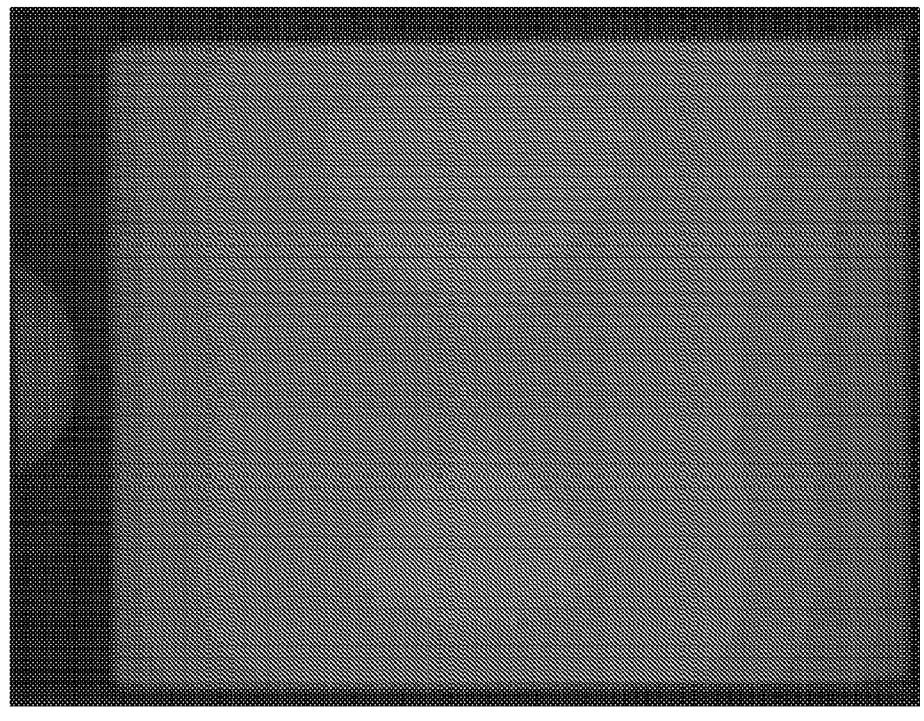
Figure 13B:
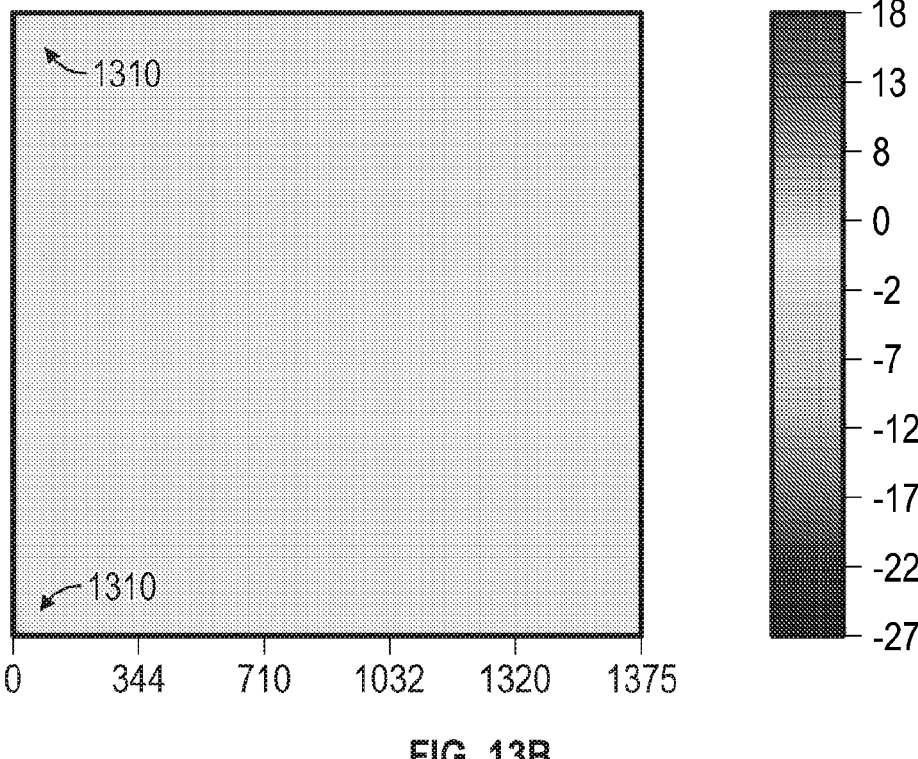
Figure 14:
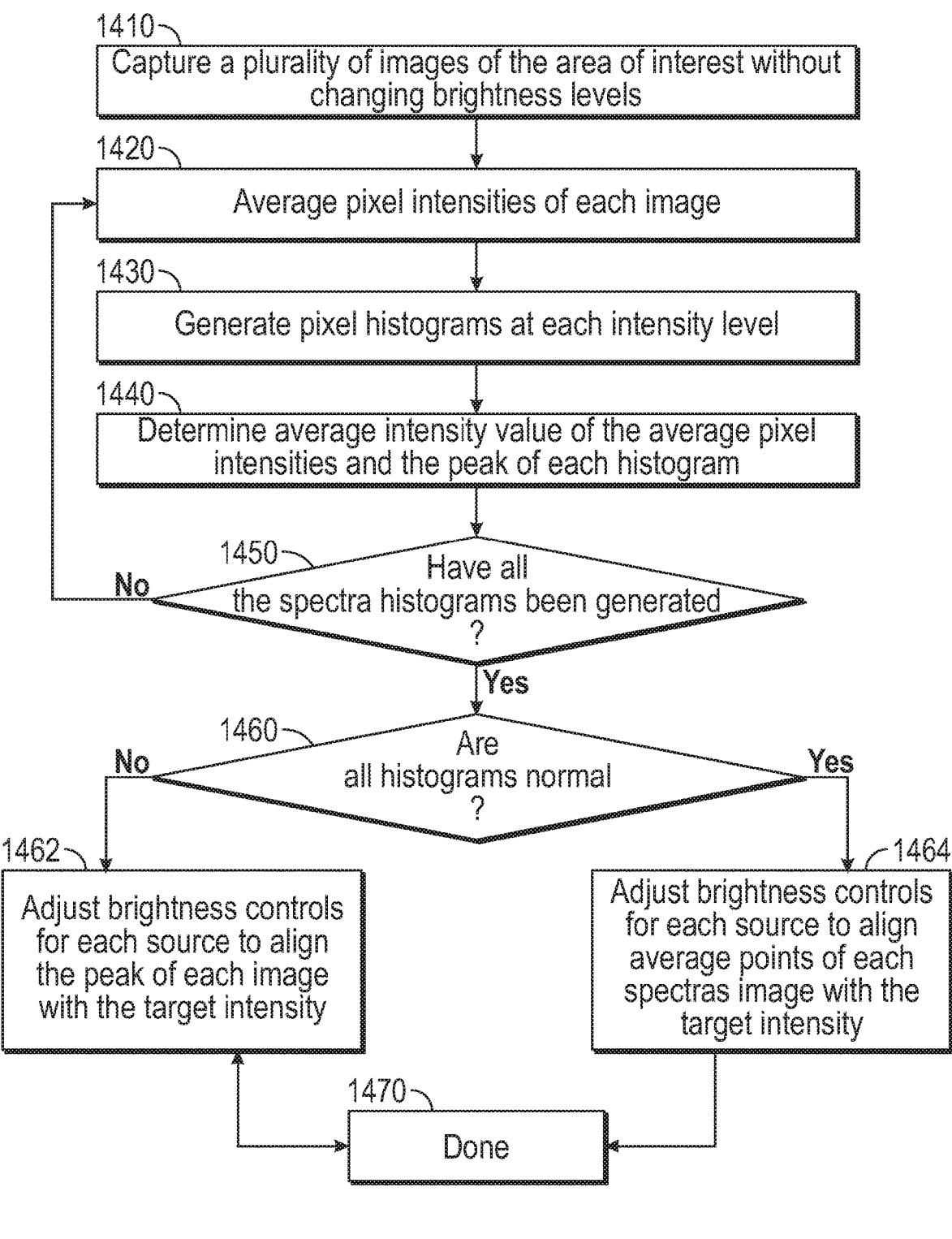
Figures 15A, 15B:
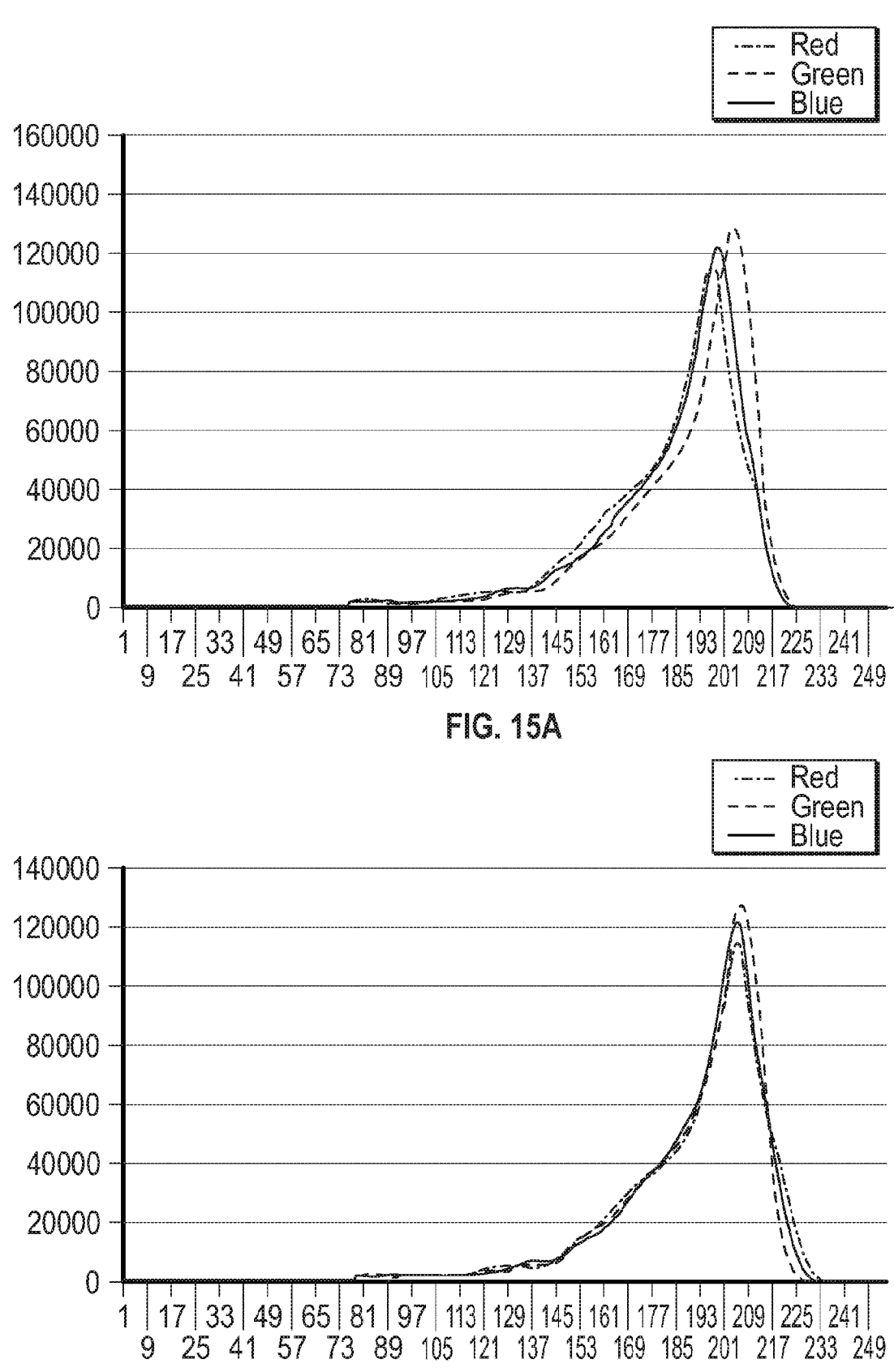
Figure 16A:
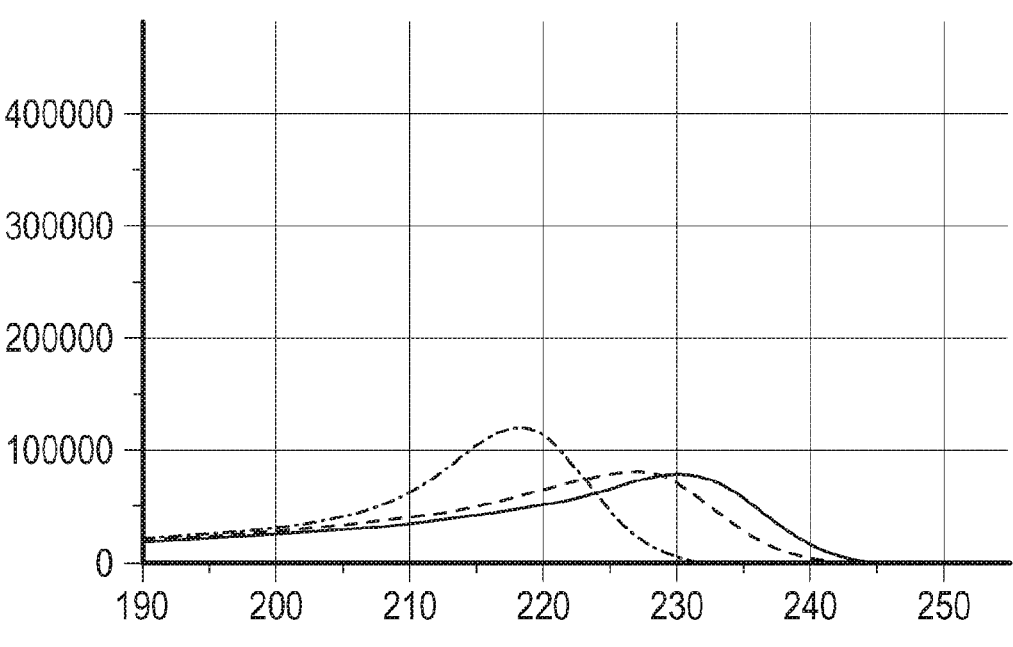
Figure 16B:
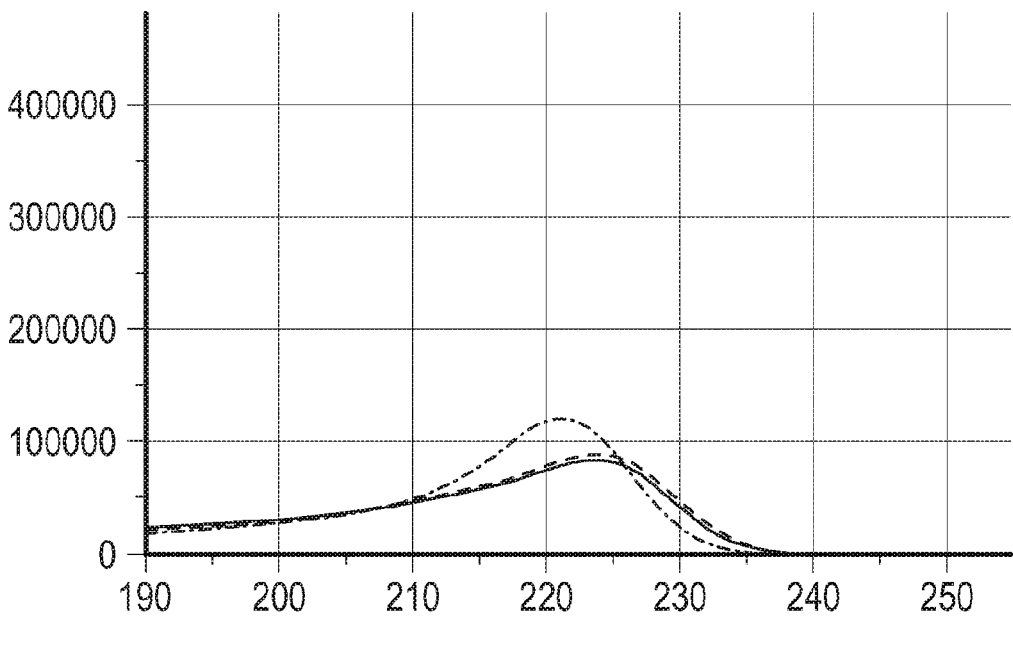
Figure 19A:
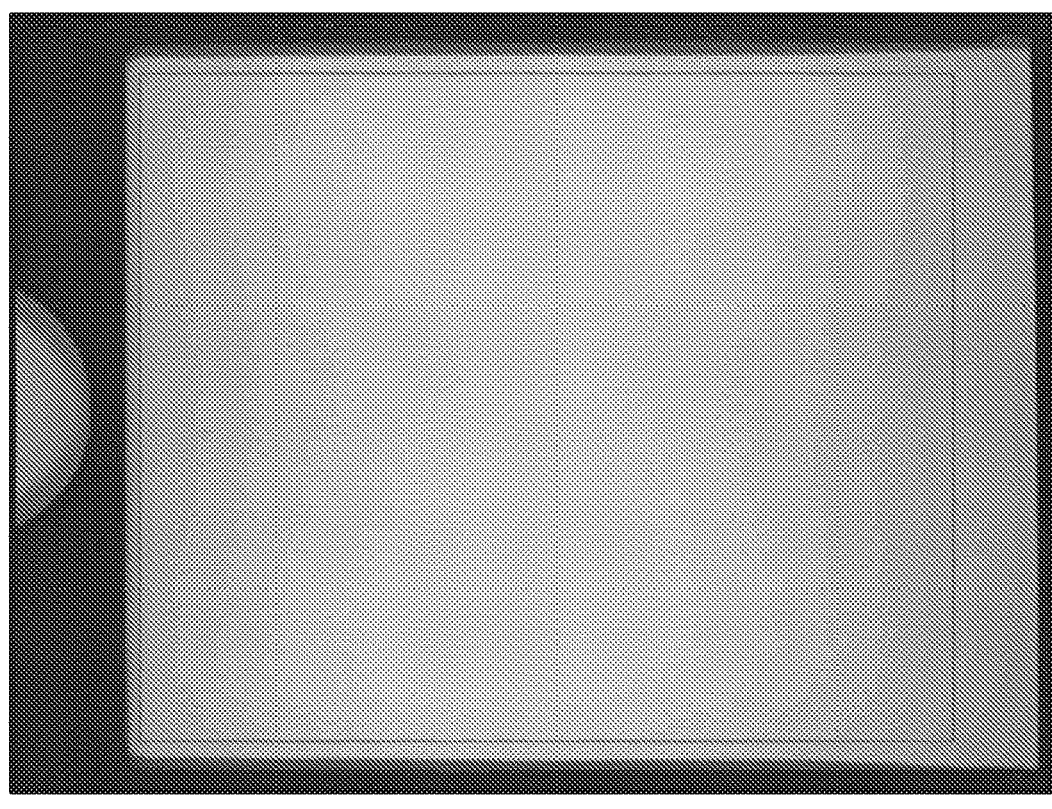
Figure 19B:
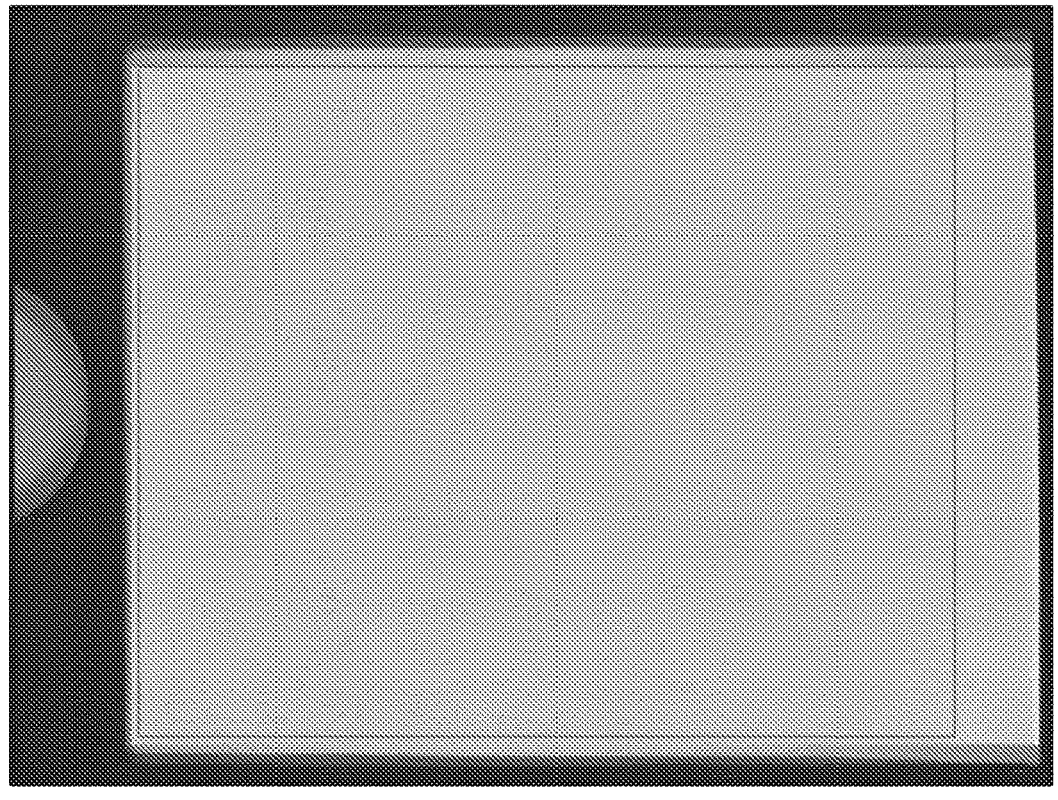
Figure 20:
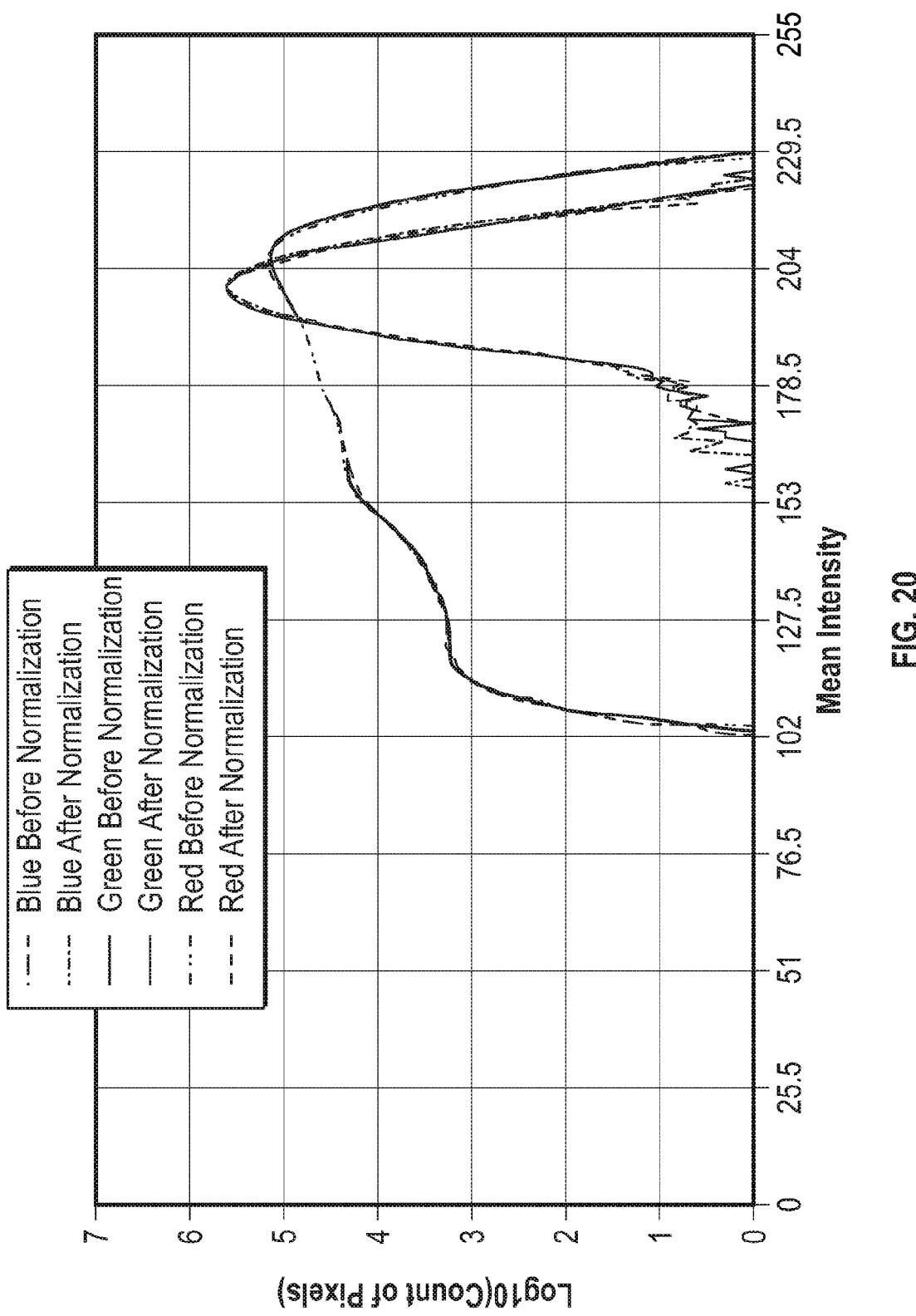
Figures 21A, 21B:
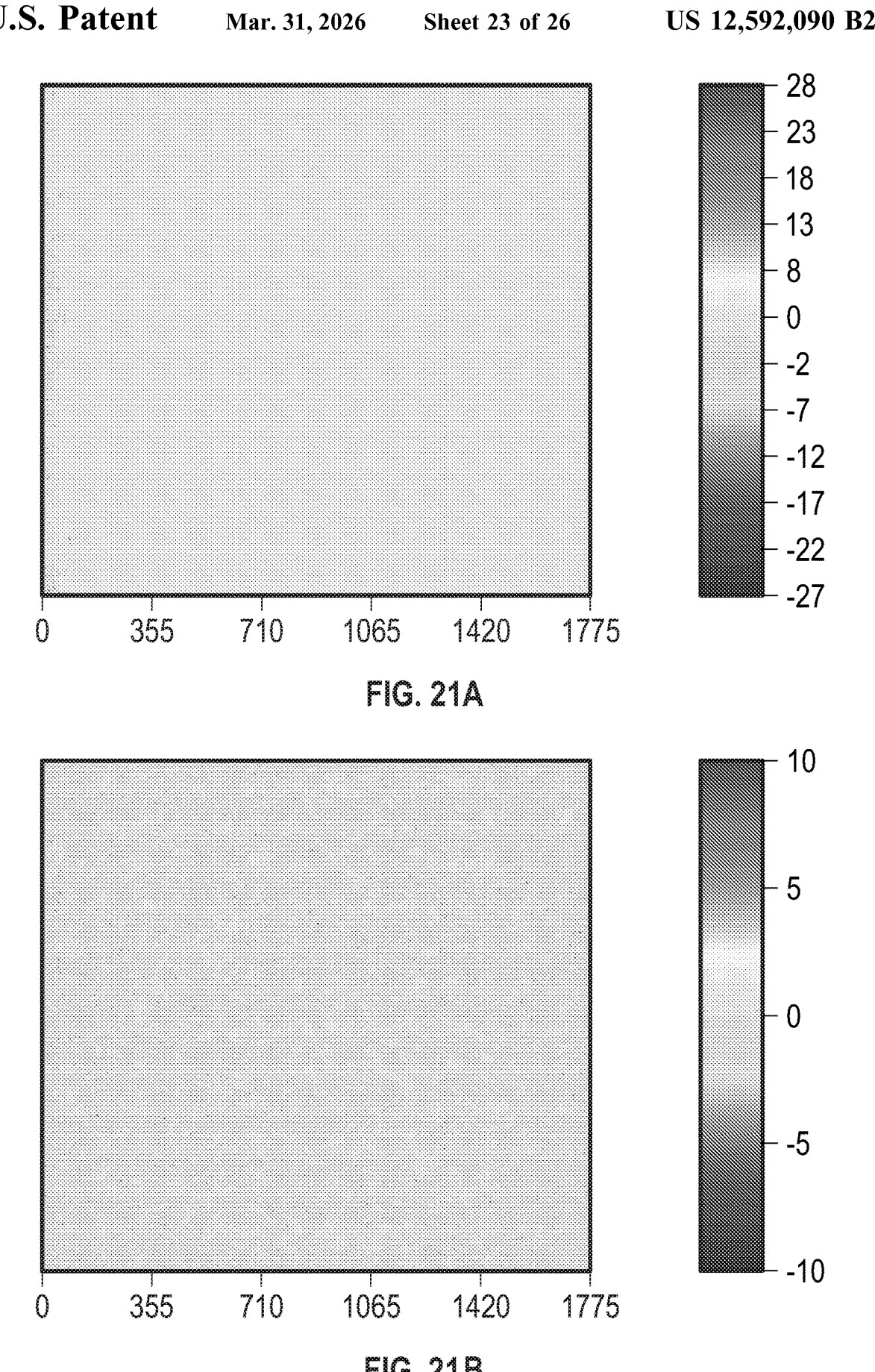
Figures 21C, 21D:
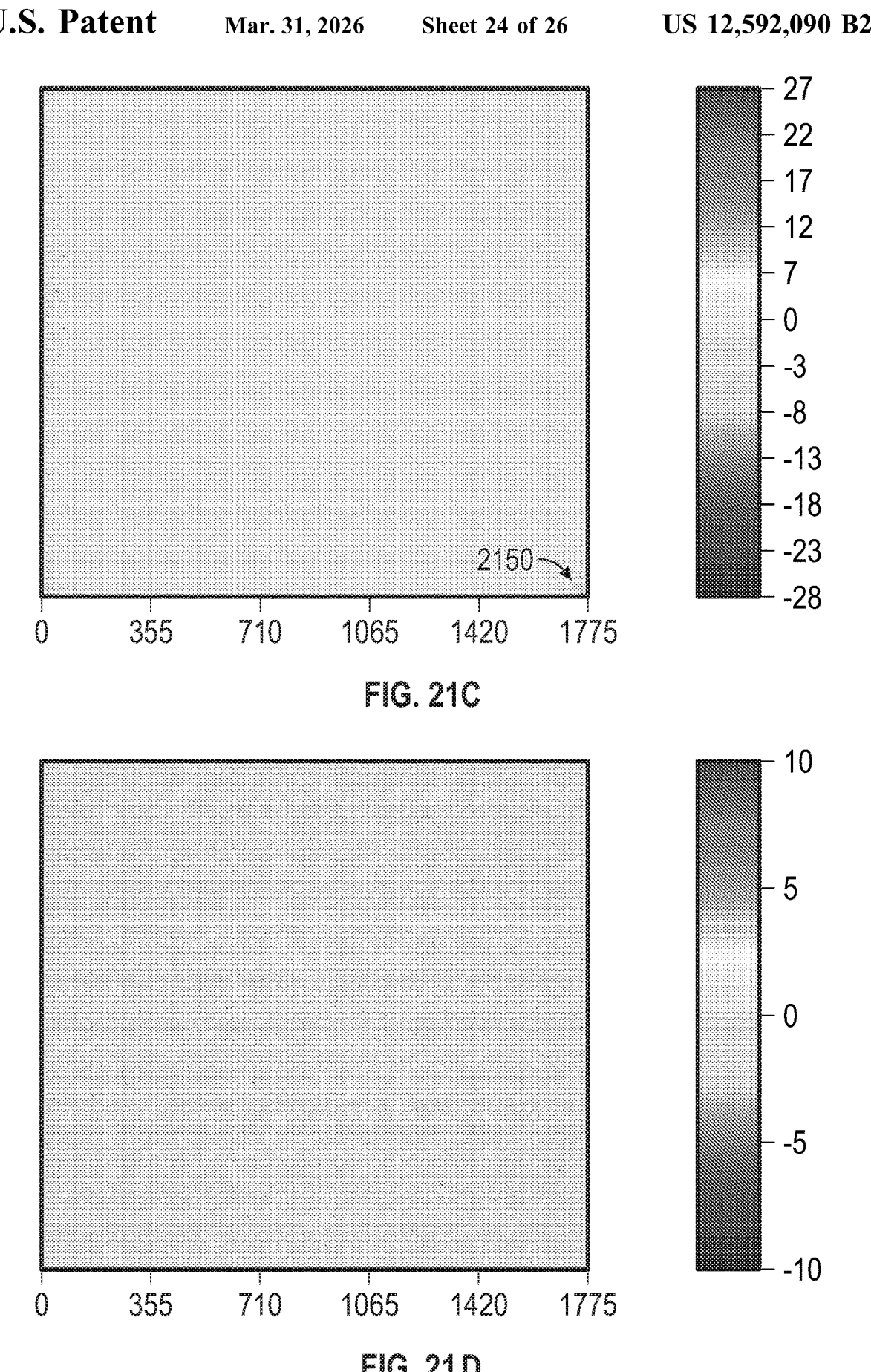
Figures 21E, 21F:
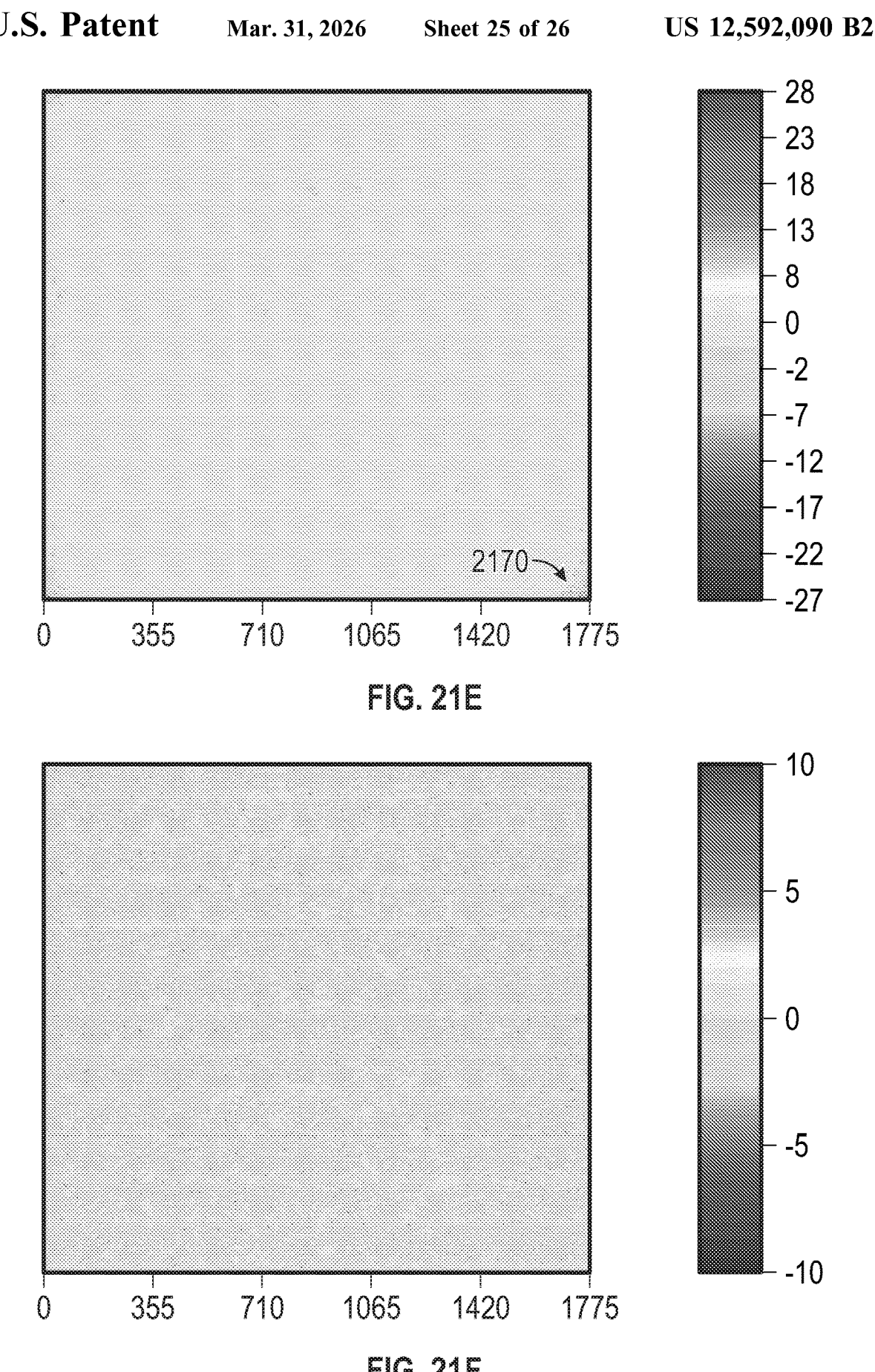
Figure 22:
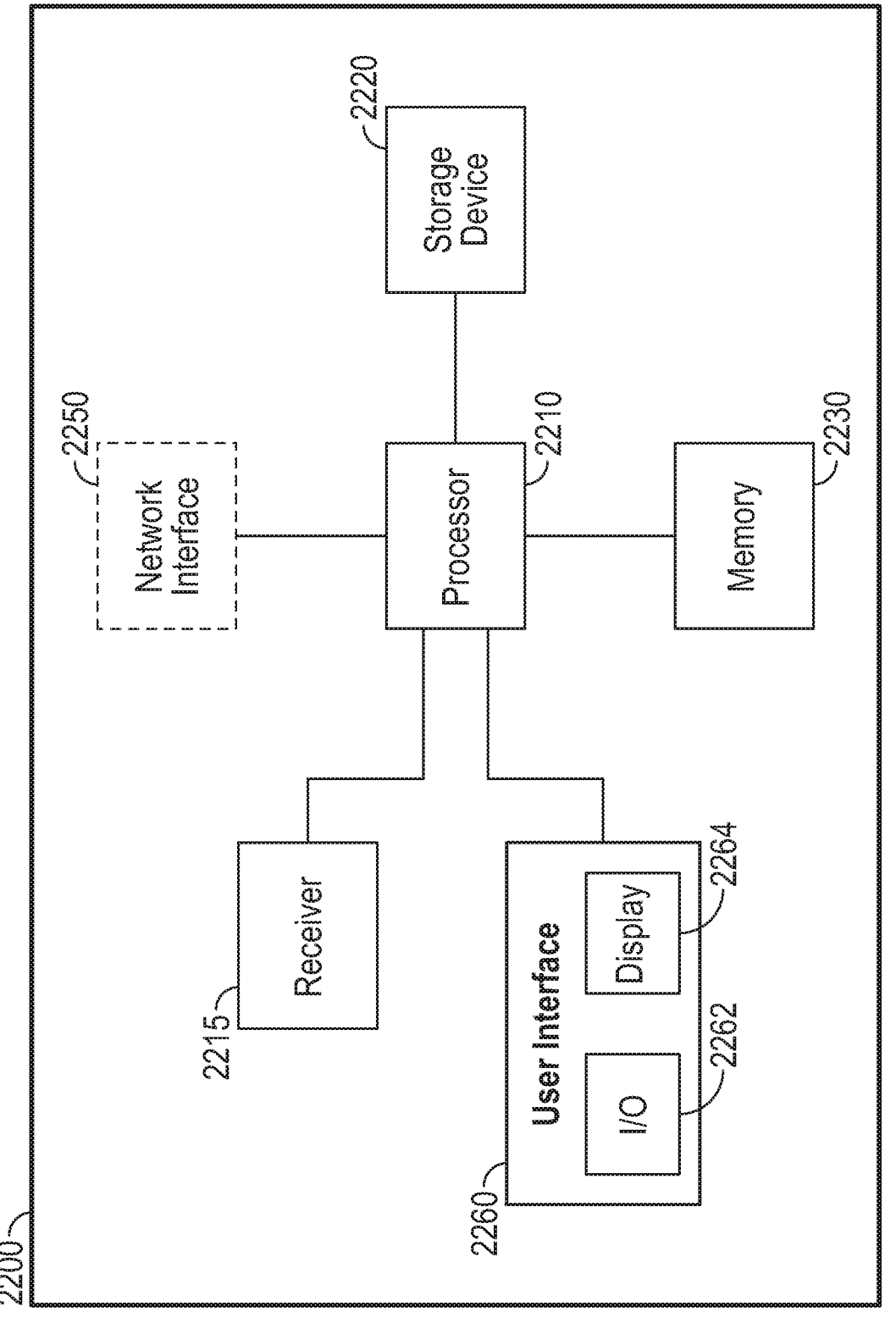

FIG. 5 shows an example of spreading colonies in accordance with embodiments described herein;

FIG. 6A shows an example of a plate having no growth in accordance embodiments described herein;

FIGS. 6B and 6C show examples of views in which the microbial growth lightens the growth media in accordance embodiments described herein;

FIG. 7 illustrates a process for compensating for variances in light output in accordance with embodiments described herein;

FIG. 8 shows a more detailed process for calculating the overall brightness control value in accordance with embodiments described herein;

FIG. 9 shows an example of a heat map for the area of interest using the overall brightness control value calculated in FIG. 8 in accordance with embodiments described herein;

FIG. 10 shows a more detailed process for calculating the individual brightness values in accordance with embodiments described herein;

FIGS. 11A-11D show an example area of interest with different individual illumination sources turned on in accordance with embodiments described herein;

FIG. 12 shows a more detailed process for calculating the calibrated brightness value in accordance with embodiments described herein;

FIG. 13A shows an example of an image taken using the final calibrated brightness values in accordance with embodiments described herein;

FIG. 13B illustrates a heat map of the image of FIG. 13A in accordance with embodiments described herein;

FIG. 14 illustrates aligning the spectra in accordance with embodiments described herein;

FIGS. 15A and 15B show examples of an unaligned normal histogram and an aligned normal histogram, respectively in accordance with embodiments described herein;

FIGS. 16A and 16B show examples of an unaligned non-normal histogram and an aligned non-normal histogram, respectively in accordance with embodiments described herein;

FIG. 17 illustrates a process for generating normalization factors in accordance with embodiments described herein;

FIG. 18 shows an example of how normalization can be used to produce a uniform image on a 5×5 Sliding Window in accordance with embodiments described herein;

FIGS. 19A and 19B show example images using just the calibrated illumination system described herein;

FIG. 20 shows an example histogram that explains the distribution of light for each red, green and blue channels and the impact of flat field normalization on the image uniformity in accordance with embodiments described herein;

FIGS. 21A-21F show heatmap representations for each of the red, green and blue channels before and after normalization in accordance with embodiments described herein; and FIG. 22 illustrates A high-level block diagram of s system configured to implement the processes described herein.

The figures are rendered primarily for clarity and, as a result, are not necessarily drawn to scale. Moreover, various structure/components, including but not limited to fasteners, electrical components (wiring, cables, etc.), and the like, may be shown diagrammatically or removed from some or all of the views to better illustrate aspects of the depicted embodiments, or where inclusion of such structure/components is not necessary to an understanding of the various exemplary embodiments described herein. The lack of illustration/description of such structure/components in a particular figure is, however, not to be interpreted as limiting the scope of the various embodiments in any way.

DETAILED DESCRIPTION

The food industry routinely monitors the levels of indicator groups of microorganisms. These organisms are considered quality and hygienic indicators and can pose health hazards to humans A common method of quantifying indicator organisms is using plate counts (colony counts). This is done by culturing target microorganisms on suitable growth media such as dry film or agar plates and counting the colonies. Millions of colony counts are done across the food industry globally by food producers, reference labs, food processors, and manufacturers. Colony counts may be done at multiple stages including on incoming materials, in process products, finished products, and/or environmental samples taken from within the food processing environment.

Counting colonies on growth media is very complex and can greatly benefit from improvements in the quality of the growth media images. Examples of unique challenges and requirements in this space which make this a complex effort include but are not limited to: growth media interpretation challenges and accuracy requirements by colony counting devices. Due to these requirements, a vast amount of data is involved in developing robust systems. The variety of appearances and features which can occur on the growth media makes colony interpretation challenging for both human operators and automated colony counting solutions.

The organisms cultured on the growth media may be discriminated from the background of a wide variety of samples. These samples may include one or more of produce, dairy products, meat and poultry, confectionary, processed foods, raw ingredients, and/or environmental samples from food production facilities. Human counters are generally used to scan or count bacterial colonies, or the amount of a particular biological agent on a biological growth plate. Using an imaging device that automatically detects and/or counts bacterial colonies and/or other biological agents may improve the accuracy, efficiency, and/or consistency of the colony detection and/or counting. For example, a food sample or laboratory sample can be placed on a biological growth plate, and then the plate can be inserted into an incubation chamber. After incubation, the biological growth plate can be placed into the imaging device for automated detection and enumeration of bacterial growth. The imaging device can automate the detection and enumeration of bacteria or other biological agents on a biological growth plate, and thereby improve the biological testing process by reducing human error.

Figure 1A:
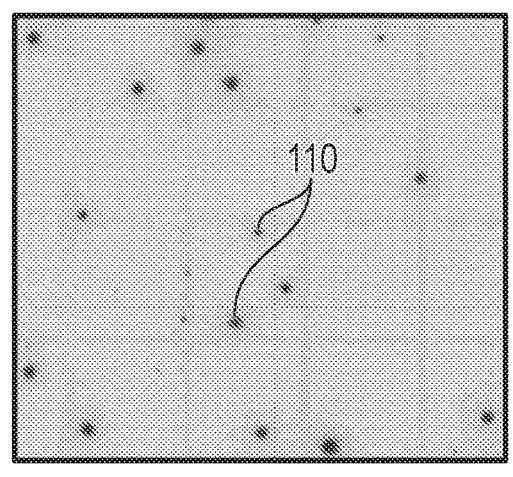
FIGS. 1A-1C show growth medias having background material on the media which interfere with interpretation by manual counters and devices in accordance with embodiments described herein.
Figure 1B:
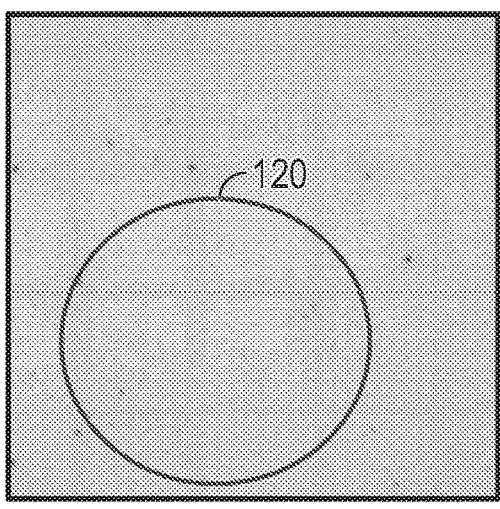
Figure 1C:
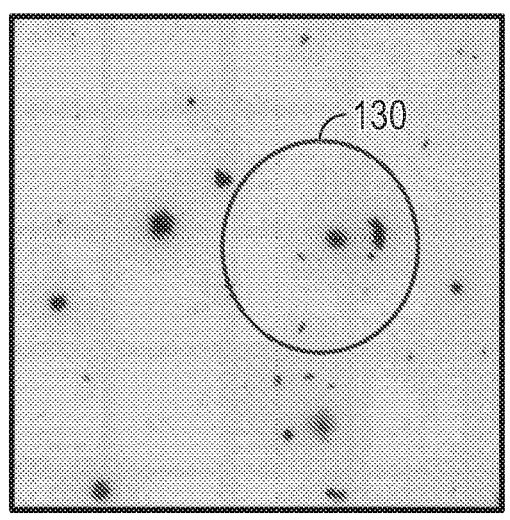

The samples deposit background material on the media (fibers, particles, colors) which interfere with interpretation by manual counters and devices as shown in the examples of FIGS. 1A-1C. FIG. 1A illustrates examples of background material 110 on the media. FIG. 1B shows an example of colonies 120 without background material. FIG. 1C shows a growth media with a mix 130 of particles and colonies on the growth media.

Figure 2A:
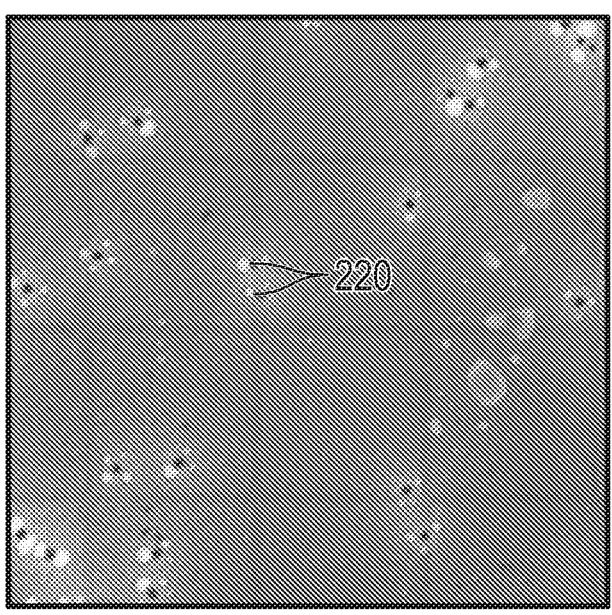
FIGS. 2A-2D illustrate different types of varieties of colony features in accordance with embodiments described herein.
Figure 2B:
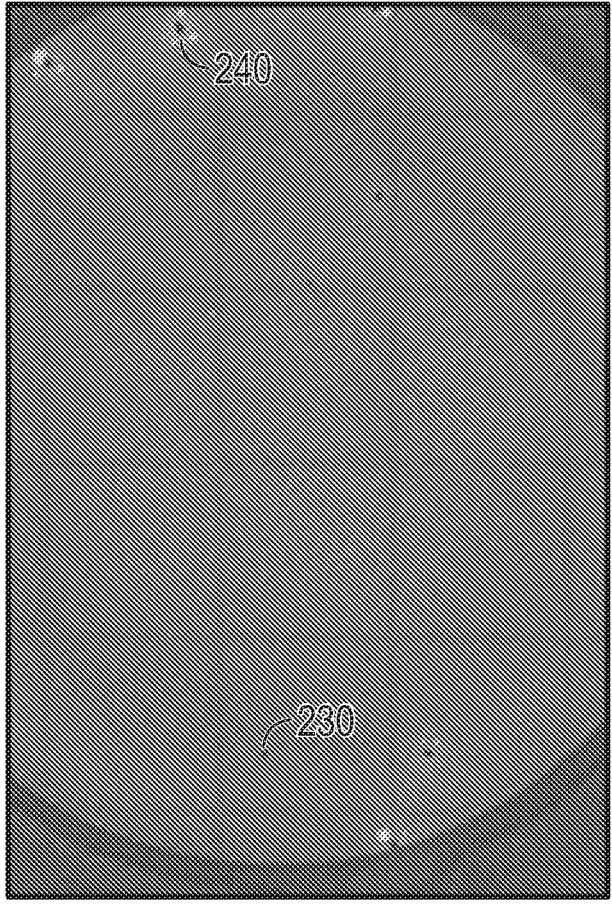
Figure 2C:
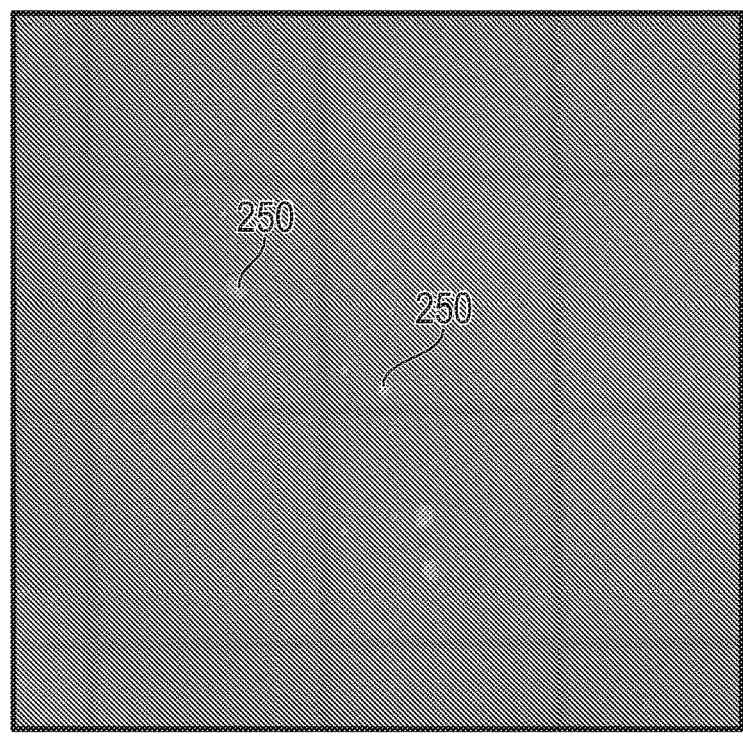
Figure 2D:
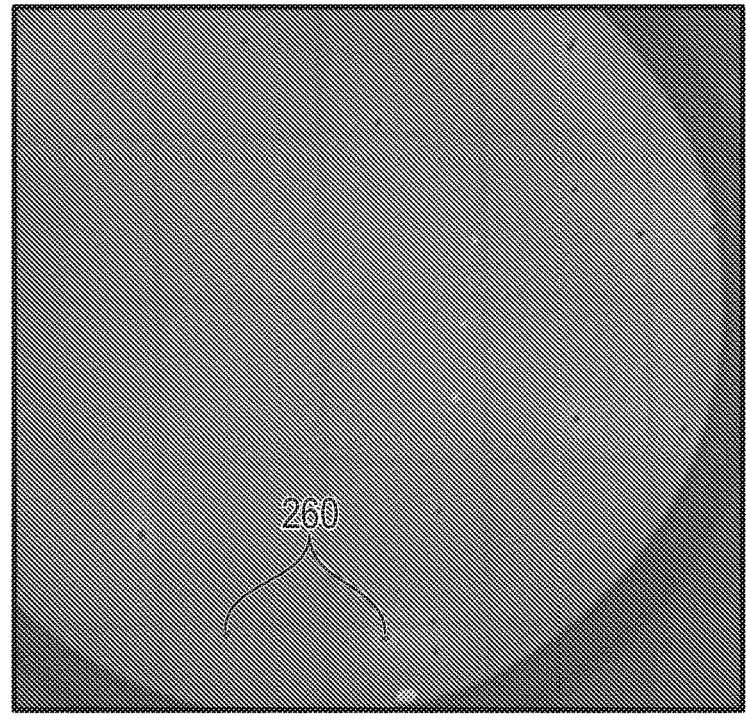

There is an immense amount of variety in colony features which include size, shape, color, gas bubble production, zone production, etc. Certain media types are used to culture multiple types of organisms In these cases, colony features must be identified so relevant colonies can be distinguished from other types of colonies. FIGS. 2A-2D illustrate different types of varieties of colony features. In FIG. 2A, colonies producing gas bubbles 210 on the growth media is shown. There may be a mixture of colonies producing gas bubbles 240 and colonies not producing gas 230 as shown in FIG. 2B. It may be useful to distinguish between these different types of colonies. According to various configurations, there may be irregular bubbles 250 on the growth media that is not associated with gas as shown in FIG. 2C. It may be useful to differentiate between gas bubbles and bubbles that are not associated with gas so that the bubbles that are not associated with agas are not included in a colony count. According to various configurations, colonies may produce acid zones 260 are varying intensities on the growth media as shown in FIG. 2D. It may be useful to differentiate between colonies that produce acid zones and colonies that do not produce acid zones.

Figure 3:
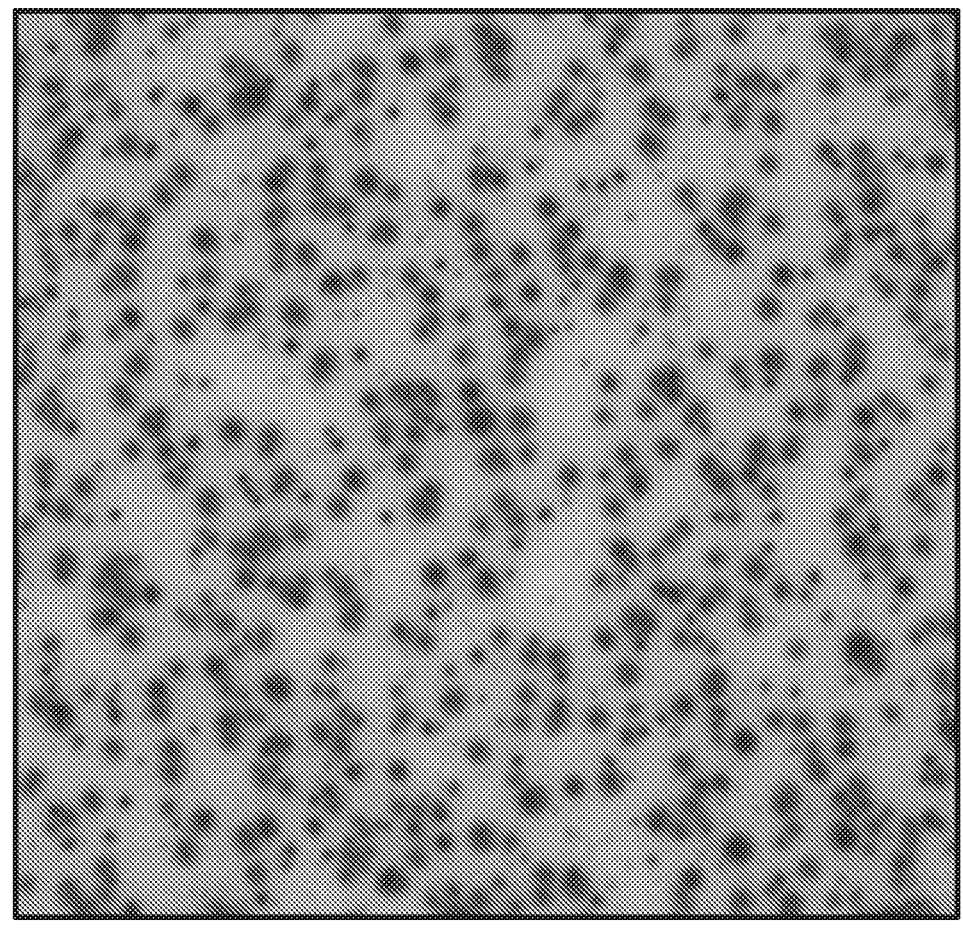
FIG. 3 illustrates an example of different morphologies of colonies that may occur when colony counts are high and/or the colonies are arrayed in close proximity to each other on the media in accordance with embodiments described herein.

FIG. 3 illustrates an example of different morphologies of colonies that may occur when colony counts are high and/or the colonies are arrayed in close proximity to each other on the media, for example. It may be useful to identify and/or differentiate between all of the colonies having different morphologies. It may be difficult to differentiate the different morphologies when the colonies are close together.

Figure 4:
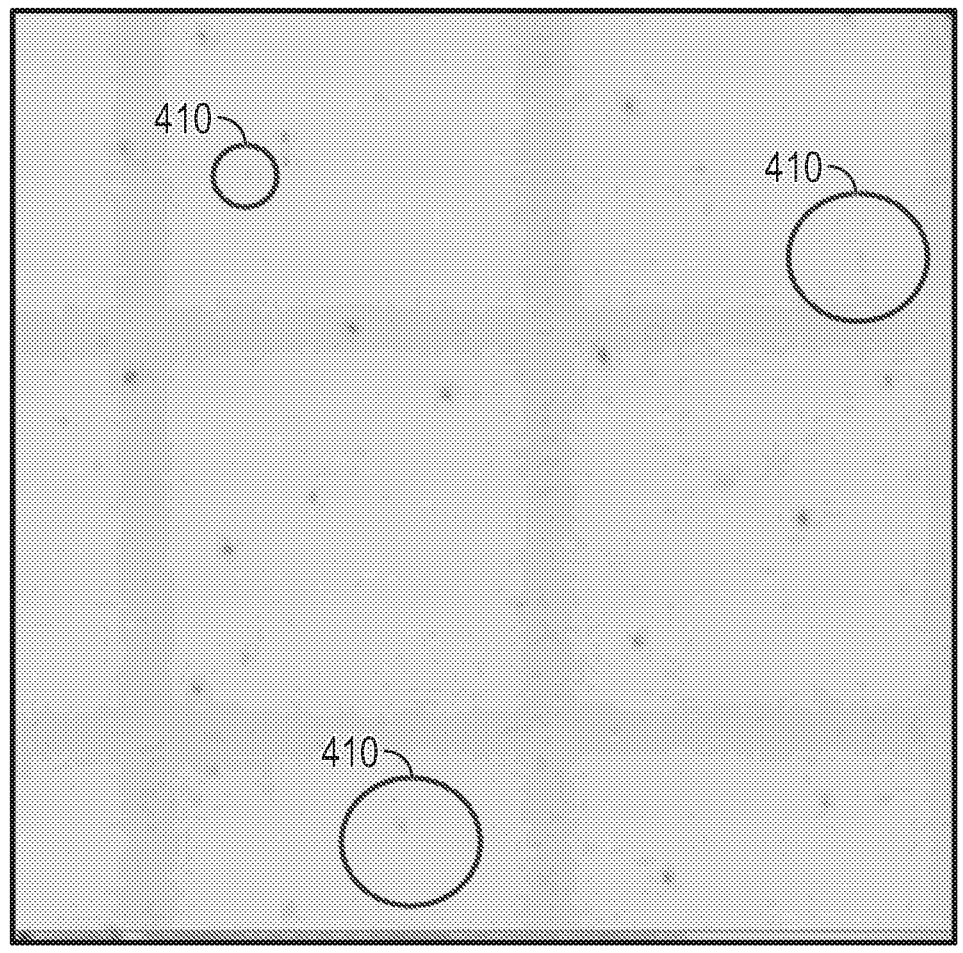
FIG. 4 shows colonies that are relatively small and/or pale when compared to the background media in accordance with embodiments described herein.

In some cases, the colonies may be relatively small and/or pale 410 when compared to the background media as shown in FIG. 4. This may make it difficult to detect the presence of colonies.

In some configurations, the colonies may spread, obscure the growth media, and/or change the appearance of the media. This type of growth may affect regions of the media or the entire growth plate. These situations also make it difficult to detect growth. FIG. 5 shows an example of spreading colonies.

FIG. 6A shows an example of a plate having no growth. FIGS. 6B and 6C show examples of views in which the microbial growth lightens the growth media. In the cases of FIGS. 6A-6C it may be difficult to differentiate any bacterial growth from the growth media.

The examples described in FIGS. 1A-6C show some of the complexity and challenges that needed to overcome by a colony counting device. The consequences of incorrect result might be recalls, rejected product, significant losses, harm to brand reputation, and/or harm to consumers.

Devices used to illuminate the growth media to detect microbial growth may be subject to variances in output from light sources. Compensating for these variances in light sources, diffusion of the light, reflection of the light, lens spatial efficiency, and/or camera response to may be useful to generate a very consistent response to light levels in the image for a colony enumeration device. A consistent brightness image allows for accurate bacterial colony identification and/or classification results because each localized colony area may have a constant response to separate colonies from food samples. Devices and methods described herein may be used to differentiate between colonies from other contamination in the sample including pH differences and/or other sources that could cause changes to the background of the media. Embodiments described herein involve compensating for differences in light source output and response of the image capture system to the light that they generate. The image capture system may include numerous components besides the light sources. For example, the image capture system may include one or more reflectors, lenses, cameras, and optical paths that may be impacted by differences in light sources. Compensating for differences in light source output allows for an even image response so that changes in the media can be accurately detected. The processes described herein may be completed once, in the factory, for example, and/or may be repeated in the field. For example, the processes described herein may be repeated on a regular basis and/or on as as-needed basis as determined by a user.

FIG. 7 illustrates a process for compensating for variances in light output in accordance with embodiments described herein. An area of interest on a growth media is determined 710. The area of interest may also be referred to herein as the region of interest (ROI). The area of interest may include any area on the growth media that comprises a subject of interest. For example, the area of interest may include an area on the growth media that comprises bacterial growth. The growth media may include biological growth plates, for example.

An overall brightness control value that generates at least one image that substantially matches a target intensity at the area of interest for a plurality of illumination sources is calculated 720. The target intensity may be a fixed value chosen to ensure sufficient intensity range exist above this target value such that bright images can still contain information useful to enumeration. The target value allows for images that are less than saturated and does not cause a significant number of pixels to have a maximum of 255. The target intensity may be chosen by evaluating an expected family of images and determining the range of the maximum brightness expected.

Various references herein are made to the terms "brightness" and "intensity." It is to be understood that "brightness" is generally used to refer to light output by the illumination sources and "intensity" is used to refer to a lightness of images captured using the illumination sources. The illumination sources can be any suitable illumination device. For example, the illumination sources may include light-emitting diodes (LEDs), incandescent devices, bio-luminescent devices, lasers, reflected sunlight, combustion devices (such as oil lamps or candle), and/or florescent devices. According to various configurations, calculating the overall brightness control value comprises adjusting a brightness of all illumination sources for the spectra simultaneously to a brightness level at or below the target intensity.

A plurality of images of the area of interest at increasing brightness values are iteratively captured starting at a common brightness below the target intensity. Mean intensities may be captured for each image and the overall brightness control value may be calculated based on the mean.

Individual brightness values for each illumination source of the plurality of illumination sources are calculated 730 by individually adjusting a brightness of each illumination source to generate at least one image that substantially matches the target intensity in each respective illumination sources area of influence. According to various configurations described herein, calculating the individual brightness value comprises, for each illumination source of the spectra, iteratively capturing a plurality of images of the area of interest of each illumination source at increasing brightness levels starting at a brightness level below the brightness control value. According to various configurations, the images are captured with each illumination source being the only illumination source turned on. In some cases, the plurality of images are captured starting at a brightness level such that the intensity of the image is significantly below the target level with each illumination source turned on one at a time. Mean intensities for each captured image of the area of influence for the illumination source turned on may be computed and the individual brightness value for each illumination source may be calculated based on the mean.

A calibrated brightness value for each illumination source may be determined 740 based on the overall brightness control value and the individual brightness values. According to various embodiments described herein, determining the calibrated brightness value for each illumination source comprises calculating a difference between the target intensity value and the individual intensities at each individual brightness levels of the area of influence for that light source. According to various embodiments, determining the calibrated brightness value for each illumination source is based on an image intensity with each illumination source turned on at the respective individual brightness value and an intensity that each illumination source generates within each respective area of influence when turned on alone.

According to various embodiments described herein, a percent change used to compensate for the difference of each individual brightness value may be calculated. A plurality of images are captured of the area of interest. Mean intensities may be captured for each captured image and the calibrated brightness value for each illumination source may be determined based on the mean and the percent change values. According to various configurations, using the mean intensity of the area of interest the percent difference between the mean intensity of the area of interest and the target intensity is determined. The data captured for each individual light source to can be used to determine the amount of brightness of each light source needs to be adjusted to move its intensity the same percentage. The value that would change the intensity of the image for each individual light source the same percentage as the captured intensity versus target intensity may be the individual light source brightness value.

The steps shown in FIG. 7 may be carried out for one or more spectra. For example, the steps of FIG. 7 may be carried out for three spectra such as red, green, and blue. Red, green, and blue represent the primary chromatic colors, but other colors may be used in addition to or as an alternative to the primary chromatic colors. For example any colors from the visible, infrared, and/or ultraviolet spectras may be used.

FIG. 8 shows a more detailed process for calculating the overall brightness control value in accordance with embodiments described herein. It is to be understood that FIG. 8 and other flow diagrams shown herein may be completed for a single spectra or may be repeated for additional spectra. The area of interest where colony enumeration will be carried out is determined 810. The area of interest may be determined by identifying boundaries of the clear image area on the device image. More specifically, the area of interest for the enumeration may be found by looking for known darker areas in the image that represents boundaries of the area. The areas of darkness may be defined by one or more of a frame around the area of interest that blocks the light from the image plane or an area that is not lighted such that the back lighting only covers the enumeration area. The brightness for all illumination sources of each spectra is computed 815 to substantially match the average intensity of the area of interest to a target intensity. All of the illumination sources are adjusted 820 simultaneously to a brightness level below a target intensity level so that the brightness level can be tuned on an individual basis. According to various configurations, all of the illumination sources are adjusted simultaneously to a brightness level generating an intensity that is just below the target level.

A plurality of images are iteratively captured 830 at increasing brightness levels. The intensity at the initial brightness level for each of the captured images may be significantly below the target intensity value without causing the intensity to reach a lowest value (e.g., an intensity of 0). The lowest value may represent the lowest black that the image capturing device can observe. The brightness level may be adjusted low enough to ensure the resulting image intensity is significantly lower than the target intensity level. This low starting value may be used to properly create a linear equation representing the intensity response to any brightness. This equation is in turn used to compute the brightness that generates an intensity that best matches the target value. This lower starting point would be created by analyzing the response of a given image system and calibration conditions and setting a value that is enough below the target that any variances in the system will not cause that level to be above the target intensity. In some cases, the starting brightness is adjusted such that it is about ½ or less the target intensity. According to various configurations, the brightness levels for each subsequent image are increased using small increments. According to various configurations, the increments are small enough to provide enough points to create an accurate equation between the start and the finish. Capturing greater number of images increases the time needed. Therefore, balancing time needed and generating an accurate equation may be desired. brightness levels may be increased until an image intensity is reached that is just less than saturated. For example, the brightness may be increased until just before any pixels are white in the area of interest. A mean intensity for each of the plurality of images is computed 840. A best fit equation is created 850 using the brightness levels and the mean intensities. The best fit equation may be created using any suitable technique. For example, the best fit equation may be created using one or more of linear regression, $2^{nd}$ order curve fitting, multi-point averaging, and curve smoothing. An overall brightness control value is calculated 860 that will substantially generate the target mean intensity. According to various configurations, the overall brightness control value is calculated by solving the best fit equation for the target intensity.

It is determined 870 whether all of the overall brightness control values have been calculated for each spectra. If it is determined 870 that not all of the overall brightness control values have been calculated for all spectra, the process continues to calculate 815 brightnesses of the illumination sources for another spectra. If it is determined that all of the overall brightness control values have been calculated, the process completes 880 and the calculated overall brightness control values are used in subsequent steps.

FIG. 9 shows an example of a heat map for the area of interest using the overall brightness control value calculated in FIG. 8. As can be observed, the majority of the area of interest is relatively uniform, but some areas, especially along the perimeter, are darker than the rest of the area as shown at 910. The heat map of FIG. 9 shows uniformity. In other words, each pixel in the heat map represents an offset of intensity from the target intensity value. In FIG. 9, most of the values are offset by +1 or +2 from the target intensity value. According to various implementations, the target intensity value is about 200 so most of the heat map is close to or equal to 200. The darker areas shown in 910 represent an offset in negative. For example, one or more of the pixel intensity values in the darker areas could be offset by −9 (200−9=191) or −14 (200−14=186).

FIG. 10 shows a more detailed process for calculating the individual brightness values in accordance with embodiments described herein. The area of influence of the illumination source is determined 1010. This may be done by capturing at least one image with only the illumination source turned on and determining an area of a captured image in which an image intensity is a threshold percentage of the target intensity. In some cases, the threshold percentage may be in a range of about 85% to about 100% According to various configurations, the threshold percentage is about 95%

A plurality of images of the area of influence for the illumination source are iteratively captured 1030 at increasing brightness levels starting at a level below the overall brightness control value calculated in FIG. 8 for the spectra being tested. According to various configurations, the images are captured for one light source at a time. The brightness levels can be applied to one light source at a time and/or cycled through the entire range one light source at a time. In some cases, the images are captured starting at a brightness level that is significantly below the overall brightness control value. For example, the images may be captured starting at a brightness level that would give the image at least ½ of the target intensity, without causing the intensity to reach 0. According to various configurations, the brightness levels for each subsequent image are increased using small increments. According to various configurations, at least five images are captured with different brightnesses to create a good representative equation. The brightness levels for each captured image may be increased until an image intensity is reached that is above the target intensity value, but less than saturated. According to various configurations, the brightness levels are increased to a level significantly above the overall brightness control value. According to various configurations, the brightness levels are increased until at least two points of testing above the target intensity. The brightness levels may be increased until about 120% of the target intensity is reached without causing saturation. A mean intensity for each of the plurality of images at the area of influence for each illumination source is computed 1040. The mean intensity may be calculated for each light source in series or in parallel. A best fit equation is created 1050 using the brightness levels and the mean intensities of the individual illumination source. The best fit equation may be created using any suitable technique. For example, the best fit equation may be created using linear regression. An individual brightness value is calculated 1060 that will generate the target mean intensity at the area of influence for the individual illumination source being tested. According to various configurations, the individual brightness value is calculated by solving the best fit equation for the target mean intensity.

It is determined 1070 whether all of the individual illumination source brightness values have been calculated for the current spectra. If it is determined 1070 that all of the illumination source brightness levels have not been calculated, the process continues to calculate 1020 a brightness value for another illumination source for the current spectra being tested. If it is determined that all of the individual illumination source brightness values have been calculated, it is determined 1080 whether all of the individual illumination source brightness values have been calculated for all spectra. If it is determined that all of the illumination source brightness values have not been calculated for all spectra, the process continues to calculate individual illumination source brightness values for other spectra. If it is determined that all of the illumination source brightness values have been completed for all spectra, the process completes and 1090 and the calculated individual brightness values are used in subsequent steps of the calibration process.

FIGS. 11A-11D show an example area of interest with different individual illumination sources turned on. As can be observed, the individual illumination sources have different areas of influence as evidenced by the lighter areas in different regions of the area of interest.

FIG. 12 shows a more detailed process for calculating the calibrated brightness value in accordance with embodiments described herein. All of the illumination sources are turned on 1210 at their respective individual brightness values calculated in FIG. 10.

A plurality of images are iteratively captured 1230 at substantially the same brightness level determined for each illumination source to generate an image in their area of influence matching the target intensity levels for the spectra being tested. The brightness level being used may be the same or different than that of different spectra being tested. A mean intensity for each of the plurality of images is computed 1240. An overall mean of all of the mean intensities of all of the images is determined 1250. An amount of change that is needed to reach the target intensity is calculated 1260 by subtracting the overall mean from the target intensity. A calibrated brightness value that will give the same amount of change in the intensity as that of each individual brightness value calculated in FIG. 12 is determined 1270 for each illumination source.

It is determined 1282 whether all of the calibrated brightness values have been calculated for the current spectra being tested. If it is determined 1282 that all of the calibrated brightness values have not been calculated for the current spectra, the process continues to capture 1230 more images for the current spectra being tested. If it is determined 1282 that all of the calibrated brightness values have been calculated for the current spectra, it is determined 1284 whether all of the calibrated brightness values have been calculated for all spectra. If it is determined 1284 that all of the calibrated brightness values have not been calculated for all spectra, the process continues to turn all illumination sources on at individual brightness values for the next spectra to be tested. If it is determined 1284 that all of the calibrated brightness values have been calculated for all spectra, the process completes 1290.

FIGS. 13A and 13B show an example of an image (FIG. 13A) and a heat map of the image (FIG. 13B) using the final calibrated brightness values. As can be observed in FIG. 13B, the heat map is substantially uniform with the exception of some small nonuniformities 1310 along the perimeter.

After calibration of the illumination device the spectrums may be further aligned to make the brightness to intensity response as similar as possible between spectrum and between devices. For example, intensity histograms for each spectra can be used to further refine the results. Each spectra can be aligned by slightly increasing or decreasing the brightness control for that spectra across all its illumination sources.

FIG. 14 illustrates aligning the spectra in accordance with embodiments described herein. A plurality of images of the area of interest are captured 1410. According to various configurations, the plurality of images are captured without changing the illumination source brightness for the current spectra being tested. The pixel intensities of each image are averaged 1420 to create mean pixel intensities. A histogram of pixels at each intensity level are generated 1430 for the current spectra being captured. The mean intensity value of the mean pixel intensities and the peak of each histogram are determined 1440. It is determined 1450 whether all the spectra histograms have been generated. If it is determined 1450 that not all of the spectra histograms have been generated, a plurality of images are captured for another spectra and the process continues. If it is determined 1460 that all of the spectra histograms have been generated, it is determined 1460 whether the histograms are normal.

According to various configurations, a normal histogram occurs when the histogram peak and the average are near to each other within a threshold. If it is determined 1460 that the histogram is not normal, the brightness controls for all illumination sources for each spectra are adjusted 1462 by the same amount to substantially align the peak of each image's intensity histogram with the target intensity and the process completes 1470. If it is determined 1460 that the histogram is normal, the brightness controls for all illumination sources for each spectra are adjusted 1464 by the same amount to substantially align the average points of each spectra's image with the target intensity and the process completes 1470. FIGS. 15A and 15B show examples of an unaligned normal histogram and an aligned normal histogram, respectively. FIGS. 16A and 16B show examples of an unaligned non-normal histogram and an aligned non-normal histogram, respectively in accordance with embodiments described herein.

According to various embodiments described herein, a flat field normalization process can be used to further enhance the image quality for use in colony enumeration. Using a flat field normalization process can allow for a substantially consistent response to light levels on the growth media on a pixel scale for colony enumeration (colony counts). Reflection, diffusion, variability of camera response, etc. are fixed pattern variations which affect the quality of colony enumeration images. Flat field normalization can compensate for all the fixed pattern variations by mathematically smoothing the image to remove fixed pattern variations caused by the imaging system.

The flat field normalization process may start by creating an average of multiple images that are illuminated at previously calibrated source brightnesses according to the (1). According to various embodiments, one or more high and/or low values are thrown out and then the remaining values for that pixel from multiple images are averaged.

$$I_{avg}[m, n] = \frac{1}{L}\sum_{l=1}^{L} I_l[m, n] \tag{1}$$

Here, the m and n are offset in a two dimensional array representing the intensity values in a 2 dimension image. m is the offset in the horizontal direction and n is the offset in vertical direction usually from the upper left corner. $I_{avg}[m, m]$ is average value of multiple images at pixel value at m, n. L is the number of images being average and $I_1$ is the intensity value at pixels m,n for image 1 of the set of images. Once the average is calculated, the flat field or, in other words, smoothed image values, will be computed using the quadratic equation shown in (2).

$$I_q[m,n]=\beta_1+\beta_2 \cdot m+\beta_3 \cdot n+\beta_4 \cdot m \cdot n+\beta_5 \cdot m^2+\beta_6 \cdot n^2 \tag{2}$$

Here, $I_q$ is the smoothed image value at pixel location m, n as defined above. These smoothed values are what an even or flat response would be. The beta values are coefficients of two variable second order equation describing the smoothed image value at pixel location m,n. According to various configurations, (2) is a $2^{nd}$ order curve fitting to make each pixel have the flattest response (e.g., same response) to a set brightness level setting.

The beta values in (2) can be determined by minimizing the squared error in the equation fitting according to (3) where I is the $I_{avg}$ and $I_q$ is the computed flat field value from the above equations.

$$sq\_err = \frac{1}{M \cdot N}\sum_{m=1}^{M}\sum_{n=1}^{N}(I[m, n] - I_q[m, n])^2 \tag{3}$$

Here, sq_err is the square of the errors between the average value at each pixels and the smoothed value computed with (2). According to various configurations, sq_err is minimized to select the beta values above. M is number of pixels dimension horizontally across the image and N is the number of pixels dimension vertically down the image. Variable m and n are offsets defining a pixel position. $I_{avg}[m,n]$ is the average vales at pixel m,n and $I_q[m,n]$ is value computed with the beta values under test of the previous equation. According to various embodiments, sq-err computes the square of the difference between the average and the flat field value for each pixel in the image Minimizing this squared error creates a second order equation describing the flat field value.

Once the quadratic equation beta values are defined, a flat field gain used to multiply each pixel to reach the flat field (smoothed value) can be computed as shown in (4).

$$GainFlatField[m, n] = \frac{I_q[m, n]}{I[m, n]} \tag{4}$$

Here, the variable m and n are offsets into the pixel of the two dimension image as descried above. $I_q[m,n]$ is the equation with the calculated beta values at location m,n in the image. I[m,n] is the average pixel intensity at location m,n in the image. GainFlatField[m,n] is the ratio of the ideal $I_q$ to the average at pixel [m,n] and represents how much any pixel intensity value should be multiplied to adjust it for the flat field smoothed response.

To further fine-tune the gain to adjust the flat field gain value for consistency from device to the device, (5) may be applied to determine the overall gain. This allows for scaling the smoothed image gain such that the resultant adjust response will be to the desired target intensity.

$$GainOverall[m, n] = \frac{DesireConsistentValue}{GainFlatField * I[m, n]} \tag{5}$$

The process of generating the flat field normalization factor may involve using an optical card which represents the desired color balance and brightness. It may be desirable to use an optical card that was verified by an industry standard instrument. The normalization factor is generated for each color channel (spectra). For example, the normalization factor may be generated for each of the red, blue, and green color channels in a system utilizing these three spectra.

The process shown in FIG. 17 may be used to generate the normalization factors. While the example shown in FIG. 17 describes a system having red, blue, and green channels, it is to be understood that this process can apply to any number of color channels and/or different color channels than are listed here. An instrument that has the illumination systems calibrated is used 1710. The illumination system may be calibrated according to embodiments discussed herein and/or using one or more different processes. All of the color channels are properly set using the calibration process. In this example, all three channels (red, blue, and green) are set A monochrome image of an optical card for each of the color channels is captured 1720. All of the monochrome images from the color channels are combined. In the case where only one color channel is used, this step may be skipped. In this example, the monochrome images are combined into an RGB24 image. The steps of capturing 1720 the monochrome images and combining 1730 the monochrome images are repeated multiple times In this example, multiple white card RGB24 images are created. The white card may be a medium (e.g., piece of paper) that has a substantially balanced or nearly balanced reflectivity for each of the spectra being calibrated. If the medium is not substantially balanced, the amount out of balance may be compensated for to align each spectra. As described herein, the region of interest (ROI) is shown 1750 as the region of bacterial growth on the media. While, this example uses bacterial growth as the ROI, it is to be understood that other types of growth in combination with or as an alternative to the bacterial growth may be used to define the ROI.

The normalization factor for each of the images is calculated 1760 using (6).

For index in range (0, #of images):

$$\text{norm\_factor[index,:,:]=medianBlur(flat\_field\_images[inex],filter\_kernel\_size=5]} \tag{6}$$

The mean of the Normalization factors is computed 1770 as shown in (7).

$$\text{Norm\_factor=mean(norm\_factor,axis=0)} \tag{7}$$

The mean calculated from (7) may be used as the instruments normalization factor and will be used to normalize all images captured by the instrument.

According to various embodiments described herein, normalization of each captured image can be performed by dividing each pixel value of the captured image by respective pixel of the normalization factor. FIG. 18 shows an example of how normalization can be used to produce a uniform image on a 5×5 Sliding Window on a per pixel basis. In this example, intensity values corresponding to each pixel in the captured image 1810 is shown. Each of the pixels is divided by their respective normalization factor 1820 to create an output image 1830 having normalized intensity values.

FIGS. 19A and 19B show example images using just the calibrated illumination system described herein (19A) and using the calibrated illumination system in addition to the flat field normalization process. It can be observed that the center region of the ROI of the image in FIG. 19B is substantially uniform throughout as compared to the uneven and not uniform ROI as evidenced by the darker region on the left and right edges of FIG. 19A.

FIG. 20 shows an example histogram that explains the distribution of light for each red, green and blue channels and the impact of flat field normalization on the image uniformity in accordance with embodiments described herein. Distribution of pixel intensity before flat field normalization is in a range of about 102 to about 230. After flat field normalization, the distribution of pixel intensity is reduced to a range of about 155 to about 225. According to various embodiments, the distribution of pixel intensity is reduced to a range of about 178 to about 220

FIGS. 21A-21F show heatmap representations for each of the red, green and blue channels before and after normalization in accordance with embodiments described herein. Specifically, FIG. 21A shows a red channel heat map before normalization FIG. 21B illustrates the red channel heat map after Normalization. FIG. 21C shows a blue channel heat map before Normalization. FIG. 21D illustrates the blue channel heat map after normalization. As can be observed by this example, the non-uniformity 2150 in the corner is substantially eliminated in the heat map after normalization shown in FIG. 21D. FIG. 21E shows a green channel heat map before normalization. FIG. 21F illustrates the green channel heat map after Normalization As can be observed by this example, the non-uniformity 2170 in the corner is substantially eliminated in the heat map after normalization shown in FIG. 21D.

The above-described methods can be implemented on a computer using well-known computer processors, memory units, storage devices, computer software, and other components. A high-level block diagram of such a computer is illustrated in FIG. 22. Computer 2200 contains a processor 2210, which controls the overall operation of the computer 2200 by executing computer program instructions which define such operation. It is to be understood that the processor 2210 can include any type of device capable of executing instructions. For example, the processor 2210 may include one or more of a central processing unit (CPU), a graphical processing unit (GPU), a field-programmable gate array (FPGA), and an application-specific integrated circuit (ASIC). The computer program instructions may be stored in a storage device 2220 (e.g., magnetic disk) and loaded into memory 2230 when execution of the computer program instructions is desired. Thus, the steps of the methods described herein may be defined by the computer program instructions stored in the memory 2230 and controlled by the processor 2210 executing the computer program instructions. The computer 1500 may include one or more network interfaces 2250 for communicating with other devices via a network. The computer 2200 also includes a user interface 2260 that enables user interaction with the computer 1500. The user interface 2260 may include I/O devices 2262 (e.g., keyboard, mouse, speakers, buttons, etc.) to allow the user to interact with the computer. Such input/output devices 2262 may be used in conjunction with a set of computer programs in accordance with embodiments described herein. The user interface also includes a display 2264. According to various embodiments, FIG. 22 is a high-level representation of possible components of a computer for illustrative purposes and the computer may contain other components.

EXEMPLARY EMBODIMENTS

Embodiment 1. A method, comprising:

determining an area of interest on a growth media;

calculating an overall brightness control value for a plurality of illumination sources configured to illuminate the growth media, the overall brightness control value generating at least one image that substantially matches a target intensity at the area of interest;

calculating an individual brightness value for each illumination source of the plurality of illumination sources based on the overall brightness control value by individually adjusting a brightness of each illumination source to generate at least one image that substantially matches the target intensity in each respective illumination source's area of influence; and determining a calibrated brightness value for each illumination source based on an image intensity with each illumination source turned on at the respective individual brightness value and an intensity that each illumination source generates within each respective area of influence when turned on alone.

Embodiment 2. The method of any one of embodiments 1 and 3-11, further comprising completing the steps of embodiment 1 for each spectra of a plurality of spectra.

Embodiment 3. The method of any one of embodiments 1, 2, and 4-11, further comprising:
  capturing a plurality of images of the area of interest at the calibrated brightness value;
  generating a pixel histogram of the intensities of each image at each of a plurality of brightness values based on the plurality of images;
  determining a mean and a peak of the pixel histogram
  adjusting the calibrated brightness value based on at least one of the mean and the peak of the pixel histogram.

Embodiment 4. The method of any one of embodiments 1-3 and 5-11, further comprising calculating at least one of the overall brightness control value and the individual brightness values using one or more of linear regression, $2^{nd}$ order curve fitting, multi-point averaging, and curve smoothing.

Embodiment 5. The method of any one of embodiments 1-4 and 6-11, wherein calculating the overall the brightness control value comprises:
  adjusting a brightness of all illumination sources of the plurality of illumination sources simultaneously to a brightness below the target intensity;
  iteratively capturing a plurality of images of the area of interest at increasing brightness levels starting at the brightness below the target intensity;
  computing mean intensities for each captured image; and
  determining the overall brightness control value based on the mean.

Embodiment 6. The method of any one of embodiments 1-5 and 7-11, wherein calculating the individual brightness values comprises:
  for each illumination source of the plurality of illumination source:
    iteratively capturing a plurality of images of the area of interest at increasing brightness levels starting below the overall brightness control value;
    computing mean intensities for each captured image; and
    determining the individual brightness value based on the mean.

Embodiment 7. The method of any one of embodiments 1-6 and 8-11, wherein the area of interest comprises a region of bacterial growth.

Embodiment 8. The method of any one of embodiments 1-7 and 9-11, further comprising:
  computing a normalization factor using a flat field normalization process; and
  adjusting the calibrated brightness value based on the normalization factor.

Embodiment 9. The method of embodiment 8, wherein the flat field normalization process comprises:
  capturing a monochrome image using the calibrated brightness value of each spectra of a plurality of spectra; and
  computing the normalization factor for each of the spectra using the monochrome image.

Embodiment 10. The method of any one of embodiments 1-9 and 11, wherein determining the calibrated brightness value comprises:
  calculating a difference between the target intensity and an image intensity at each individual brightness value;
  calculate a percent change value of each individual brightness value to compensate for the difference;
  capturing a plurality of images of the area of interest;
  computing mean intensities for each captured image; and determining the calibrated brightness value based on the mean and the percent change values.

Embodiment 11. The method of any one of embodiments 1-10, further comprising:
  for each illumination source of the plurality of illumination source:
    capturing at least one image with the illumination source turned on; and
    determining an area of influence by determining an area of the image in which an image intensity is a threshold percentage of the target intensity.

Embodiment 12. A system, comprising:
  a processor; and
  a memory storing computer program instructions which when executed by the processor cause the processor to perform operations comprising:
    determine an area of interest on a growth media;
    calculate an overall brightness control value for a plurality of illumination sources configured to illuminate the growth media, the overall brightness control value generating at least one image that substantially matches a target intensity at the area of interest;
    calculate an individual brightness value for each illumination source of the plurality of illumination sources based on the overall brightness control value by individually adjusting a brightness of each illumination source to generate at least one image that substantially matches the target intensity in each respective illumination source's area of influence; and
  determine a calibrated brightness value for each illumination source based on an image intensity with each illumination source turned on at the respective individual brightness value and an intensity that each illumination source generates within each respective area of influence when turned on alone.

Embodiment 13. The system of any one of embodiments 12 and 14-19, wherein the illumination source comprises one or more of a light emitting diode (LED), an incandescent device, and a fluorescent device.

Embodiment 14. The system of any one of embodiments 12, 13, and 15-19, wherein the processor is further configured to:
  capture a plurality of images of the area of interest at the calibrated brightness value;
  generate a pixel histogram of the intensities of each image at each of a plurality of brightness values based on the plurality of images; and
  determine a mean and a peak of the pixel histogram.

Embodiment 15. The system of any one of embodiments 12-14 and 16-19, wherein the processor is further configured to calculate at least one of the overall brightness control value and the individual brightness values using linear regression.

Embodiment 16. The system of any one of embodiments 12-15 and 17-19, wherein calculating the overall the brightness control value comprises:
  adjusting a brightness of all illumination sources of the plurality of illumination source s simultaneously to a brightness below the target intensity;
  iteratively capturing a plurality of images of the area of interest at increasing brightness levels starting at the brightness below the target intensity;
  computing mean intensities for each captured image; and
  determining the overall brightness control value based on the mean.

Embodiment 17. The system of any one of embodiments 12-16, 18, and 19, wherein calculating the individual brightness values comprises:

for each illumination source of the plurality of illumination source:

iteratively capturing a plurality of images of the area of interest at increasing brightness levels starting below the brightness control value;

computing mean intensities for each captured image; and determining the individual brightness value based on the mean.

Embodiment 18. The system of any one of embodiments 12-17 and 19, wherein the area of interest comprises a region of bacterial growth.

Embodiment 19. The system of any one of embodiments 12-18, wherein the processor is further configured to:

compute a normalization factor using a flat field normalization process; and adjust the calibrated brightness value based on the normalization factor.

Embodiment 20. A non-transitory computer readable medium storing computer program instructions for designing microstructures, the computer program instructions when executed by a processor cause the processor to perform operations comprising:

determining an area of interest on a growth media;

calculating an overall brightness control value for a plurality of illumination sources configured to illuminate the growth media, the overall brightness control value generating at least one image that substantially matches a target intensity at the area of interest;

calculating an individual brightness value for each illumination source of the plurality of illumination sources based on the overall brightness control value by individually adjusting a brightness of each illumination source to generate at least one image that substantially matches the target intensity in each respective illumination source's area of influence; and determining a calibrated brightness value for each illumination source based on an image intensity with each illumination source turned on at the respective individual brightness value and an intensity that each illumination source generates within each respective area of influence when turned on alone.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The various embodiments described above may be implemented using circuitry and/or software modules that interact to provide particular results. One of skill in the computing arts can readily implement such described functionality, either at a modular level or as a whole, using knowledge generally known in the art. For example, the flowcharts illustrated herein may be used to create computer-readable instructions/code for execution by a processor. Such instructions may be stored on a computer-readable medium and transferred to the processor for execution as is known in the art. The structures and procedures shown above are only a representative example of embodiments that can be used to facilitate embodiments described above.

The foregoing description of the example embodiments have been presented for the purposes of illustration and description. It is not intended to be exhaustive or to limit the inventive concepts to the precise form disclosed. Many modifications and variations are possible in light of the above teachings. Any or all features of the disclosed embodiments can be applied individually or in any combination, not meant to be limiting but purely illustrative. It is intended that the scope be limited by the claims appended herein and not with the detailed description.

What is claimed is:

1. A method, comprising:

determining an area of interest on a growth media using an imaging device; wherein said imaging device is configured to capture an image for automated detection and enumeration;

wherein said imaging device is configured to calculate an overall brightness control value for a plurality of illumination sources configured to illuminate the growth media, the overall brightness control value generating at least one image that substantially matches a target intensity at the area of interest;

wherein said imaging device is configured to calculate an individual brightness value for each illumination source of the plurality of illumination sources based on the overall brightness control value by individually adjusting a brightness of each illumination source to generate at least one image that substantially matches the target intensity in each respective illumination source's area of influence; and wherein said imaging device is configured to determine a calibrated brightness value for each illumination source based on an image intensity with each illumination source turned on at the respective individual brightness value and an intensity that each illumination source generates within each respective area of influence when turned on alone;

wherein said imaging device is configured to capture a plurality of images of the area of interest at the calibrated brightness value and average pixel intensities of each image;

wherein calculating the overall the brightness control value comprises:

adjusting a brightness of all illumination sources of the plurality of illumination sources simultaneously to a brightness below the target intensity;

iteratively capturing a plurality of images of the area of interest at increasing brightness levels starting at the brightness below the target intensity;

computing mean intensities for each captured image; and determining the overall brightness control value based on the mean;

wherein calculating the individual brightness values comprises:

for each illumination source of the plurality of illumination source:

iteratively capturing a plurality of images of the area of interest at increasing brightness levels starting below the overall brightness control value;

computing mean intensities for each captured image; and determining the individual brightness value based on the mean; and wherein determining the calibrated brightness value comprises:

calculating a difference between the target intensity value and an image intensity at each individual brightness value;

calculate a percent change value of each individual brightness value to compensate for the difference;

capturing a plurality of images of the area of interest;

computing mean intensities for each captured image; and determining the calibrated brightness value based on the mean and the percent change values.

2. The method of claim 1, further comprising completing the steps of claim 1 for each spectra of a plurality of spectra.

3. The method of claim 1, further comprising:

generating a pixel histogram of the intensities of each image at each of a plurality of brightness values based on the plurality of images;

determining a mean and a peak of the pixel histogram; and adjusting the calibrated brightness value based on at least one of the mean and the peak of the pixel histogram.

4. The method of claim 1, further comprising calculating at least one of the overall brightness control value and the individual brightness values using one or more of linear regression, $2^{nd}$ order curve fitting, multi-point averaging, and curve smoothing.

5. The method of claim 1, wherein the area of interest comprises a region of bacterial growth.

6. The method of claim 1, further comprising:

computing a normalization factor using a flat field normalization process; and adjusting the calibrated brightness value based on the normalization factor.

7. The method of claim 6, wherein the flat field normalization process comprises:

capturing a monochrome image using the calibrated brightness value of each spectra of a plurality of spectra; and computing the normalization factor for each of the spectra using the monochrome image.

8. The method of claim 1, further comprising:

for each illumination source of the plurality of illumination source:

capturing at least one image with the illumination source turned on; and determining an area of influence by determining an area of the image in which an image intensity is a threshold percentage of the target intensity.

9. A system, comprising:

a processor; and a memory storing computer program instructions which when executed by the processor cause the processor to perform operations comprising:

determine an area of interest on a growth media using said processor;

wherein said processor is configured to calculate an overall brightness control value for a plurality of illumination sources configured to illuminate the growth media, the overall brightness control value generating at least one image that substantially matches a target intensity at the area of interest;

wherein said processor is configured to calculate an individual brightness value for each illumination source of the plurality of illumination sources based on the overall brightness control value by individually adjusting a brightness of each illumination source to generate at least one image that substantially matches the target intensity in each respective illumination source's area of influence; and wherein said processor is configured to determine a calibrated brightness value for each illumination source based on an image intensity with each illumination source turned on at the respective individual brightness value and an intensity that each illumination source generates within each respective area of influence when turned on alone;

wherein said imaging device is configured to capture a plurality of images of the area of interest at the calibrated brightness value and average pixel intensities of each image;

wherein calculating the overall the brightness control value comprises:

adjusting a brightness of all illumination sources of the plurality of illumination sources simultaneously to a brightness below the target intensity;

iteratively capturing a plurality of images of the area of interest at increasing brightness levels starting at the brightness below the target intensity;

computing mean intensities for each captured image; and determining the overall brightness control value based on the mean;

wherein calculating the individual brightness values comprises:

for each illumination source of the plurality of illumination source:

iteratively capturing a plurality of images of the area of interest at increasing brightness levels starting below the overall brightness control value;

computing mean intensities for each captured image; and determining the individual brightness value based on the mean; and wherein determining the calibrated brightness value comprises:

calculating a difference between the target intensity value and an image intensity at each individual brightness value;

calculate a percent change value of each individual brightness value to compensate for the difference;

capturing a plurality of images of the area of interest;

computing mean intensities for each captured image; and determining the calibrated brightness value based on the mean and the percent change values.

10. The system of claim 9, wherein the illumination source comprises one or more of a light emitting diode (LED), an incandescent device, and a fluorescent device.

11. The system of claim 9, wherein the processor is further configured to:

capture a plurality of images of the area of interest at the calibrated brightness value;

generate a pixel histogram of the intensities of each image at each of a plurality of brightness values based on the plurality of images; and determine a mean and a peak of the pixel histogram.

12. The system of claim 9, wherein the processor is further configured to calculate at least one of the overall brightness control value and the individual brightness values using linear regression.

13. The system of claim 9, wherein calculating the overall the brightness control value comprises:

adjusting a brightness of all illumination sources of the plurality of illumination sources simultaneously to a brightness below the target intensity;

iteratively capturing a plurality of images of the area of interest at increasing brightness levels starting at the brightness below the target intensity;

computing mean intensities for each captured image; and determining the overall brightness control value based on the mean.

14. The system of claim 9, wherein calculating the individual brightness values comprises:

for each illumination source of the plurality of illumination source:

iteratively capturing a plurality of images of the area of interest at increasing brightness levels starting below the overall brightness control value;

computing mean intensities for each captured image; and determining the individual brightness value based on the mean.

15. The system of claim 9, wherein the area of interest comprises a region of bacterial growth.

16. The system of claim 9, wherein the processor is further configured to:

compute a normalization factor using a flat field normalization process; and adjust the calibrated brightness value based on the normalization factor.

17. A non-transitory computer readable medium storing computer program instructions for designing microstructures, the computer program instructions when executed by a processor cause the processor to perform operations comprising:

determining an area of interest on a growth media using said processor;

wherein said processor is configured to calculate an overall brightness control value for a plurality of illumination sources configured to illuminate the growth media, the overall brightness control value generating at least one image that substantially matches a target intensity at the area of interest;

wherein said processor is configured to calculate an individual brightness value for each illumination source of the plurality of illumination sources based on the overall brightness control value by individually adjusting a brightness of each illumination source to generate at least one image that substantially matches the target intensity in each respective illumination source's area of influence; and wherein said processor is configured to determine a calibrated brightness value for each illumination source based on an image intensity with each illumination source turned on at the respective individual brightness value and an intensity that each illumination source generates within each respective area of influence when turned on alone;

wherein said imaging device is configured to capture a plurality of images of the area of interest at the calibrated brightness value and average pixel intensities of each image;

wherein calculating the overall the brightness control value comprises:

adjusting a brightness of all illumination sources of the plurality of illumination sources simultaneously to a brightness below the target intensity;

iteratively capturing a plurality of images of the area of interest at increasing brightness levels starting at the brightness below the target intensity;

computing mean intensities for each captured image; and determining the overall brightness control value based on the mean;

wherein calculating the individual brightness values comprises:

for each illumination source of the plurality of illumination source:

iteratively capturing a plurality of images of the area of interest at increasing brightness levels starting below the overall brightness control value;

computing mean intensities for each captured image; and determining the individual brightness value based on the mean; and wherein determining the calibrated brightness value comprises:

calculating a difference between the target intensity value and an image intensity at each individual brightness value;

calculate a percent change value of each individual brightness value to compensate for the difference;

capturing a plurality of images of the area of interest;

computing mean intensities for each captured image; and determining the calibrated brightness value based on the mean and the percent change values.

* * * * *